United States Patent
Prendergast et al.

(10) Patent No.: US 6,831,063 B1
(45) Date of Patent: Dec. 14, 2004

(54) BRIDGING INTEGRATOR-2(BIN2) NUCLEIC ACID MOLECULES AND PROTEINS AND USES THEREFOR

(75) Inventors: George C Prendergast, Bala Cynwyd, PA (US); Kai Ge, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 326 days.

(21) Appl. No.: 10/069,540

(22) PCT Filed: Aug. 30, 2000

(86) PCT No.: PCT/US00/23723

§ 371 (c)(1),
(2), (4) Date: Feb. 25, 2002

(87) PCT Pub. No.: WO01/16158

PCT Pub. Date: Mar. 8, 2001

Related U.S. Application Data

(60) Provisional application No. 60/151,554, filed on Aug. 31, 1999.

(51) Int. Cl.[7] .......................... A61K 38/16; C12P 21/06; C12N 1/20; C12N 15/00; C07H 21/02
(52) U.S. Cl. ..................... 514/12; 435/69.1; 435/252.3; 435/320.1; 536/23.1
(58) Field of Search ...................... 514/12, 2; 435/69.1, 435/252.3, 320.1; 536/23.1; 530/388.26

(56) References Cited

U.S. PATENT DOCUMENTS

| | | | |
|---|---|---|---|
| 5,605,830 A | | 2/1997 | Prendergast |
| 5,723,581 A | * | 3/1998 | Prendergast et al. ........ 530/350 |
| 5,958,753 A | | 9/1999 | Prendergast |
| 6,309,820 B1 | * | 10/2001 | Sparks et al. .................. 435/6 |

OTHER PUBLICATIONS

Sequence Alignment between Applicants SEQ ID No :2, residues 23–35, 138–155 and sequences from USP 6,309, 820, 5,605,830, and 5,723,581 (pp. 2–5).*

P. Wigge et al, "The Amphiphysin Family of Proteins and Their Role in Endocytosis at the Synapse", Trends Neurosci., 21:339–344 (1998).

E. Dropcho, "Antiamphiphysin Antibodies with Small–Cell Lung Carcinoma and Paraneoplastic Encephalomyelitis", Ann. Neurol., 39(5):659–667 (May, 1996).

F. Folli et al, "Autoantibodies to a 128–kd Synaptic Protein in Three Women with the Stiff–Man Syndrome and Breast Cancer", N. Engl. J. Med., 328(8):546–551 (Feb., 1993).

D. Sakamuro et al, "BIN1 is a Novel Myc–Interacting Protein with Features of a Tumour Suppressor", Nature Genetics, 14:69–77 (Sep., 1996).

N–C. Mao et al, "The Murine Bin1 Gene Functions Early in Myogenesis and Defines a New Region of Synteny Between Mouse Chromosome 18 and Human Chromosome 2", Genomics, 56:51–58 (1999).

G. Prendergast, "Mechanisms of Apoptosis by c–Myc", Oncogene, 18:2967–2987 (1999).

R. Wechsler–Reya et al, "A Role for the Putative Tumor Suppressor Bin1 in Muscle Cell Differentiation", Mol. Cell. Biol., 18(1):566–575 (Jan., 1998).

J. Antoine et al, "Antiamphiphysin Antibodies are Associated with Various Paraneoplastic Neurological Syndromes and Tumors", Arch. Neurol., 56:172–177 (Feb., 1999).

\* cited by examiner

*Primary Examiner*—Tekchand Saidha
(74) *Attorney, Agent, or Firm*—Howson and Howson

(57) ABSTRACT

The present invention provides Bin2 sequences and proteins encoded thereby. Also provided are compositions and methods utilizing these sequences and proteins in the diagnosis and treatment of blood disorders, including hepatocarcinoma. Further provided are oligonucleotides derived from sequences encoding Bin2, as well as compositions and methods utilizing same for diagnostic and therapeutic purposes.

5 Claims, 8 Drawing Sheets

FIGURE 1A

```
gcggccgcgt cgacgggagt tggcagg atg gca gag ggc aag gca ggc ggc gcg    54
                             Met Ala Glu Gly Lys Ala Gly Gly Ala
                              1               5 gcc ggc ctc ttc gcc aag cag gtg cag aag aag ttt agc agg gcc cag      102
Ala Gly Leu Phe Ala Lys Gln Val Gln Lys Lys Phe Ser Arg Ala Gln
 10              15                  20                  25 gag aag gtg ctg cag aaa ttg ggg aaa gct gta gaa acc aaa gat gaa      150
Glu Lys Val Leu Gln Lys Leu Gly Lys Ala Val Glu Thr Lys Asp Glu
             30                  35                  40 cga ttt gaa caa agc gct agc aac ttc tac caa caa cag gca gaa ggc      198
Arg Phe Glu Gln Ser Ala Ser Asn Phe Tyr Gln Gln Gln Ala Glu Gly
             45                  50                  55 cac aag ctg tac aag gac ctg aag aac ttc ctt agt gca gtc aaa gtg      246
His Lys Leu Tyr Lys Asp Leu Lys Asn Phe Leu Ser Ala Val Lys Val
         60                  65                  70 atg cat gaa agt tca aaa aga gtg tca gaa acc ctg cag gag atc tac      294
Met His Glu Ser Ser Lys Arg Val Ser Glu Thr Leu Gln Glu Ile Tyr
         75                  80                  85 agc agc gag tgg gac ggt cat gag gag ctg aag gcc atc gta tgg aat      342
Ser Ser Glu Trp Asp Gly His Glu Glu Leu Lys Ala Ile Val Trp Asn
 90                  95                 100                 105 aat gat ctc ctt tgg gaa gac tac gag gag aaa ctg gct gac cag gct      390
Asn Asp Leu Leu Trp Glu Asp Tyr Glu Glu Lys Leu Ala Asp Gln Ala
                110                 115                 120 gta agg acc atg gaa atc tat gtt gcc cag ttc agt gaa att aag gag      438
Val Arg Thr Met Glu Ile Tyr Val Ala Gln Phe Ser Glu Ile Lys Glu
             125                 130                 135 aga att gcc aag cgg ggt cgg aaa ctc gtg gac tat gac agt gcc cga      486
Arg Ile Ala Lys Arg Gly Arg Lys Leu Val Asp Tyr Asp Ser Ala Arg
             140                 145                 150 cac cac ctg gag gca gtg cag aat gcc aag aaa gat gag gcc aag act      534
His His Leu Glu Ala Val Gln Asn Ala Lys Lys Asp Glu Ala Lys Thr
 155                 160                 165 gcc aag gca gag gaa gag ttc aac aaa gcc cag act gtg ttt gaa gat      582
Ala Lys Ala Glu Glu Glu Phe Asn Lys Ala Gln Thr Val Phe Glu Asp
 170                 175                 180                 185 ctg aac caa gaa cta cta gag gag ctg cct att ctt tat aat agt cgt      630
Leu Asn Gln Glu Leu Leu Glu Glu Leu Pro Ile Leu Tyr Asn Ser Arg
             190                 195                 200 att ggc tgc tat gtg acc atc ttc caa aac att tcc aac ttg agg gat      678
Ile Gly Cys Tyr Val Thr Ile Phe Gln Asn Ile Ser Asn Leu Arg Asp
         205                 210                 215
```

FIGURE 1B

```
gtc ttc tac agg gaa atg agc aag ctg aac cac aat ctc tac gag gtg    726
Val Phe Tyr Arg Glu Met Ser Lys Leu Asn His Asn Leu Tyr Glu Val
        220                 225                 230 atg agc aaa ctg gag aag caa cat tcc aat aaa gtc ttt gtg gtg aag    774
Met Ser Lys Leu Glu Lys Gln His Ser Asn Lys Val Phe Val Val Lys
        235                 240                 245 gga ctg tca agc agc agc agg cgc tct tta gtc att tct ccc cca gtt    822
Gly Leu Ser Ser Ser Ser Arg Arg Ser Leu Val Ile Ser Pro Pro Val
250                 255                 260                 265 cga aca gct aca gtc tcc agt cct ctt acc tca cct act agt ccc tct    870
Arg Thr Ala Thr Val Ser Ser Pro Leu Thr Ser Pro Thr Ser Pro Ser
                270                 275                 280 aca ctt tcc ttg aag agt gag agt gaa tct gtc tca gca act gaa gat    918
Thr Leu Ser Leu Lys Ser Glu Ser Glu Ser Val Ser Ala Thr Glu Asp
                285                 290                 295 ctg gca cct gat gca gcc caa ggg gaa gac aat tct gag atc aag gag    966
Leu Ala Pro Asp Ala Ala Gln Gly Glu Asp Asn Ser Glu Ile Lys Glu
                300                 305                 310 ctc tta gaa gag gag gaa ata gag aag gaa gga tct gaa gca agc tcc   1014
Leu Leu Glu Glu Glu Glu Ile Glu Lys Glu Gly Ser Glu Ala Ser Ser
        315                 320                 325 tct gag gaa gat gac cct cta cca gcc tgc aat ggc ccc gcc cag gcc   1062
Ser Glu Glu Asp Asp Pro Leu Pro Ala Cys Asn Gly Pro Ala Gln Ala
330                 335                 340                 345 cag ccc tct cct acc act gag agg gcc aag tcc cag gag gaa gtt ctc   1110
Gln Pro Ser Pro Thr Thr Glu Arg Ala Lys Ser Gln Glu Glu Val Leu
                350                 355                 360 ccc agc tcc aca act cca tca cca ggc gga gcc ctg agc cct tca ggg   1158
Pro Ser Ser Thr Thr Pro Ser Pro Gly Gly Ala Leu Ser Pro Ser Gly
                365                 370                 375 cag cct tca tca tct gcc aca gaa gta gtc ctc cga acc cgc acc gca   1206
Gln Pro Ser Ser Ser Ala Thr Glu Val Val Leu Arg Thr Arg Thr Ala
        380                 385                 390 agt gaa gga tct gaa caa cca aag aag aga gcc tct atc cag agg acc   1254
Ser Glu Gly Ser Glu Gln Pro Lys Lys Arg Ala Ser Ile Gln Arg Thr
        395                 400                 405 tca gca ccc cct agt agg cct cct cca ccc aga gcc act gca agc ccc   1302
Ser Ala Pro Pro Ser Arg Pro Pro Pro Arg Ala Thr Ala Ser Pro
410                 415                 420                 425
```

FIGURE 1C

```
agg ccc tcc tca ggg aac ata cct tcc agc cct aca gcc tct gga ggg    1350
Arg Pro Ser Ser Gly Asn Ile Pro Ser Ser Pro Thr Ala Ser Gly Gly
                430                 435                 440 ggt tca ccc acc agc cct agg gcc tcc ttg ggg act ggg act gca agt    1398
Gly Ser Pro Thr Ser Pro Arg Ala Ser Leu Gly Thr Gly Thr Ala Ser
            445                 450                 455 cct agg acc tcc cta gag gtc tct cct aat cca gaa cca cca gag aag    1446
Pro Arg Thr Ser Leu Glu Val Ser Pro Asn Pro Glu Pro Pro Glu Lys
        460                 465                 470 cca gta aga act cct gag gcc aaa gaa aat gaa aac atc cac aat cag    1494
Pro Val Arg Thr Pro Glu Ala Lys Glu Asn Glu Asn Ile His Asn Gln
    475                 480                 485 aac cct gaa gaa ctt tgt act tcc ccc acc tta atg aca tct cag gtt    1542
Asn Pro Glu Glu Leu Cys Thr Ser Pro Thr Leu Met Thr Ser Gln Val
490                 495                 500                 505 gct tca gag cct gga gag gca aag aag atg gaa gac aag gaa aag gat    1590
Ala Ser Glu Pro Gly Glu Ala Lys Lys Met Glu Asp Lys Glu Lys Asp
                510                 515                 520 aat aag ctt atc tca gct gac tcc tcg gag ggc caa gac cag ctt caa    1638
Asn Lys Leu Ile Ser Ala Asp Ser Ser Glu Gly Gln Asp Gln Leu Gln
                525                 530                 535 gtc tcc atg gta cca gaa aac aac aac ctc aca gca cct gaa cct caa    1686
Val Ser Met Val Pro Glu Asn Asn Asn Leu Thr Ala Pro Glu Pro Gln
            540                 545                 550 gaa gag gta tcc aca agt gaa aat cca caa ctc tgaagagaaa ctaccaagac  1739
Glu Glu Val Ser Thr Ser Glu Asn Pro Gln Leu
        555                 560 tcctcctgcc ccaaacctcg ccagagaagc tcttcaacca gagggtatag gtcagaggga  1799
tataagagcc agcatccatc cctgggttct cagtaggaat gctggtgctg tctaaagacc  1859
tggcattaat ggaggcggag gagcagcctt acgggaggga tggagggagg caggctgggg  1919
agaagagaac attagactca gggaatattt aattctggtt ttagcattat tagaataaga  1979
ctttatacat taactaaagt ggagctttaa tcactataaa aagcaaaagt atntatagac  2039
acagacactt gcctatacag agacataacc acacacactc agaggatagt gaacaaatct  2099
gtctttgact tacgacccat tttgcaagac ttaaagccga aagaacacat tttcagattg  2159
ttaaataaag tctgattctg actaaaaaaa aaaaaaa                           2196
```

FIG. 2

| | | |
|---|---|---|
| Bin 2: | MAE - GKAGGAAGLFAKQVQKKFSRAQEKVLQ | 30 |
| | ||| | | || | |||| |||||||| | |
| Bin 1: | MAEMGSKGVT AGKIASNVQKKLTRAQEKVLQ | 31 |

| | | |
|---|---|---|
| Bin2: | KLGKAVETKDERFEQSAS NFYQQQAEGHKLY | 61 |
| | ||||| ||||| ||| || | || | | |
| Bin1: | KLGKADETKDEQFEQCVQNFNKQLT EGTRLQ | 62 |

| | | |
|---|---|---|
| Bin2: | KDLKNFLSAVKVMHESS KRVSETLQEI Y SSEW | 93 |
| | ||| | || |||.|| |||| | | | |
| Bin1: | KDLRTYLASVKAMHEASKKLNECLQEVYEPDW | 94 |

| | | |
|---|---|---|
| Bin2: | DGHEELKA IVWNNDLLWE DYEEKLA DQAVR | 123 |
| | | | | |||||| || || ||| | |
| Bin1: | P GRDEANKIAE NNDLLWM DYHQKLVDQALL | 124 |

| | | |
|---|---|---|
| Bin2: | TMEI YVAQFSEIKE RIAKRGRKLVDYDSARHH | 155 |
| | || | || || ||||| |||||| ||||||| | |
| Bin1: | TMDT YLGQFPDIKS RIAKRGRKLVDYDSARHH | 156 |

| | | |
|---|---|---|
| Bin2: | LEAVQNA - KKDEAKT AKAEEE FNKAQTVFED | 185 |
| | | | | ||| ||| |||||| ||| ||| |
| Bin1: | YESL QTAK KKDEAKI AKAEEE LI KAQKVFEE | 187 |

| | | |
|---|---|---|
| Bin 2: | L NQELL EELPI LY NSR I GCYVTI FQNISNLRD | 227 |
| | | | |||| | ||| | || || | | |
| Bin 1: | MNVDLQEELPS LWNSRVGFYVNTFQS IAGLEE | 226 |

| | | |
|---|---|---|
| Bin2: | VFYREMSKLNHNLYEVMSKLEKQHSNKVFVVKG | 250 |
| | | |||||| || | |||||| | || |
| Bin1: | NFHKEMSKLNQNLNDVLVGLEKQHGSNTFTVKA | 252 |

Figure 4A

Bin1   AQKVFEEMNVDLQEELP--SLWNSRVGFYVNIFQSIAGLEENFHK-EMSKLNQNLNDVLVGLEKQHGSNTFTVKAQ----U3-U2-MED

AQ VFE++N +L EELP L+ NSR+G YV FQ I+ L+ F++ EMSKLN+NL +V+ LEKQH+ F VK

Bin2   AQTVFEDLNQELLEELP--ILYNSRIGCYVTIFQNISNLRDVFYR-EMSKLNHNLYEVMSKLEKQHSNKVFVVKGLSSSSRRSLVISPPVRTATVS

AQ F.D+ LE+ ++YN +GC++T +Y ++L N + IS+L++ S ++ G ++ R A

DAXX   AQDAFRDVGIRLQERRIHLDLIYN--FGCIHLTDDYRPGVDPALSYPVSARRLRENRILALSRLDQVISFYAMLQDGGEEGKKKK------RRARLD

Bin    SPLTSPTSPSTLSLKSESESVSATEDLAPDAAQGEDNSEIKELL---EEEEIEKEGSEASSSEEDEPL

P+ +P SL S + + P A+++E +E E EEEE E+E EA+ SEE+E L

DAXX   GPSSHSANPPEPSLDSGEGPIGMASQGCPSASRAETDDEDDEESDEEEEEEEEEEATDSEEEEDL

BRIDGING INTEGRATOR-2(BIN2) NUCLEIC ACID MOLECULES AND PROTEINS AND USES THEREFOR

CROSS-REFERENCE TO RELATED APPLICATIONS

This is a 371 of PCT/US/00/23723, filed Aug. 30, 2000, which claims the benefit of the priority of U.S. Patent Application No. 60/151,554, filed Aug. 31, 1999, now abandoned.

This work was supported in part by Grant Nos. DAMD17-96-1-6324 and DAMD 17-98-1-8508 from the US Army Breast and Prostate Cancer Research Programs. The US government has certain rights in this invention.

FIELD OF THE INVENTION

This invention relates generally to cancer diagnosis and therapy, and more specifically, to cancers associated with over- or underexpression of Bin1 or other members of the BAR family of adaptor proteins.

BACKGROUND OF THE INVENTION

Bin1/Amphiphysin/RVS (BAR) proteins are a family of adaptor proteins implicated in a diverse set of cellular processes, including tumnorigenesis, cell survival, differentiation, and nerve synaptic activity. BAR proteins share a common N-terminal BAR domain also termed the RVS domain. While BAR proteins share a common domain (BAR), they appear to have divergent physiological functions. As one example, amphiphysin is a neuronal protein of this family which is implicated in synaptic vesicle endocytosis [Wigge and McMahon, *Trends Neurosci.* 21: 339–344 (1998)]. Amphiphysin is also a paraneoplastic autoimmune antigen in cancers of the breast, lung, and other tissues [Antoine et al, *Arch. Neurol.* 56: 172–177 (1999); Dropcho, Ann. Neurol. 39: 659–667(1996); Folli et al., *N. Engl. J. Med.* 328: 546–51 (1993)].

Bin1 (Bridging INtegrator-1) is a second, ubiquitous BAR protein that was initially identified in mammalian cells through its ability to interact with and inhibit the oncogenic properties of c-Myc [Sakarnuro et al., Nature Genet. 14: 69–77 (1996)]. Ubiquitous Bin1 isoforms that localize to the nucleus have tumor suppressor properties and have been implicated in growth control, differentiation, and programmed cell death [Mao et al., *Genomics* 56: 51–58 (1999); Prendergast, *Oncogene* 18: 2966–2986 (1999); Sakamuro et al. 1996, cited above; Wechsler-Reya et al., *Mol. Cell. Biol.* 18: 566–575 (1998)].

Other members of the BAR family include the yeast proteins RVS 167 and RVS161, which are believed to have some negative role in cell growth regulation. There exists a need in the art for compositions and methods useful for diagnosis and treatment of conditions characterized by inappropriate cell growth control, or disorders affecting cell survival, differentiation, endocytosis, and actin organization.

SUMMARY OF THE INVENTION

The present invention provides a novel member of the Bin1/Amphiphysin/RVS (BAR) proteins, termed herein Bin2. Bin2 proteins, nucleic acids, and other Bin2 compositions of the invention have a variety of uses related to regulation of cell growth control, cell survival, differentiation, endocytosis and actin organization, as well as for the diagnosis and treatment of conditions associated with aberrant cell behavior.

In one aspect, the present invention provides a Bin2 protein. In one desirable embodiment, the protein has the 564 amino acid sequence of SEQ ID NO:2. In another embodiment, the present invention provides a Bin2 peptide or protein selected from the group consisting of a fragment of Bin2 comprising at least 8 amino acids in length. In one embodiment a fragment of this invention is at least 8 contiguous amino acids in length and is selected from amino acids 1 to 13 of SEQ ID NO:2. In another embodiment, a fragment of this invention is at least 14 amino acids in length and includes amino acids 23 to 35 of SEQ ID NO:2, and preferably amino acids 2345 of SEQ ID NO: 2. In still another embodiment, a fragment includes amino acids 138–155 of SEQ ID NO:2 and comprises at least 19 amino acids in length. In still another embodiment, a fragment includes amino acids 179–336, or a smaller fragment of at least 8 amino acids contained therein. Still other fragments may be selected from the sequence. In yet another embodiment, the invention provides analogs or homologs of SEQ ID NO:2. In still another embodiment, the invention provides a fusion protein comprising the amino acid sequence of SEQ ID NO: 2, a fragment, analog or homolog thereof, and a fusion partner. In still a further embodiment, the invention provides a deletion protein comprising the amino acid sequence of SEQ ID NO:2 with one to twenty amino acids deleted therefrom.

In another aspect, the present invention provides a Bin2 nucleic acid sequence. Desirably, the Bin2 nucleic acid sequence encodes a protein or fragment of the invention (such as those mentioned above) and contains SEQ ID NO:1 or a fragment thereof. In one embodiment, the Bin2 nucleic acid sequence hybridizes to the sequence of SEQ ID NO:1 under stringent conditions. In another embodiment, the invention provides a nucleic acid sequence complementary to the nucleic acid sequence of SEQ ID NO:1. In still another embodiment, the invention provides a nucleic acid sequence encoding a fusion protein of the invention. In a further embodiment, the invention provides an allelic variant of any of the Bin2 nucleic acid sequences of the invention. In still another embodiment, the nucleic acid sequence is an antisense sequence to the sequences described above.

In a further aspect, the invention provides a vector comprising a Bin2 nucleic acid sequence of the invention under the control of regulatory sequences which direct expression of the Bin2 protein.

In still another aspect, the invention provides a host cell transformed with the vector of the invention.

In yet a further aspect, the invention provides a diagnostic reagent comprising a Bin2 nucleic acid sequence of the invention and a detectable label which is associated with said sequence. Methods of diagnosing conditions associated with inappropriate functional levels, the loss of expression of Bin2 or altered expression of Bin2, e.g., cancers, which use this reagent are also provided.

In still a further aspect, the invention provides a diagnostic reagent comprising a Bin2 protein or peptide of the invention and a detectable label which is associated with that protein. Also provides are methods of using this reagent and/or the Bin2 protein for diagnosing cancers associated with inappropriate expression (e.g., overexpression or underexpression or altered expression) of Bin1, to which Bin2 binds. This method involves the steps of contacting a sample from a human or animal to be diagnosed with the Bin2 protein of the invention, or the diagnostic reagent containing this protein, whereby in the presence of Bin1 in the sample, a complex is formed between Bin1 and the Bin2 protein or reagent, and analyzing for the presence of said complex.

In yet another aspect, the invention provides an isolated anti-Bin2 antibody which is specific for the Bin2 protein of the invention.

In still another aspect, the invention provides a diagnostic reagent comprising the anti-Bin2 antibody of the invention and a detectable label. Further provided by the invention is a method of diagnosing cancer or hyperplastic disease characterized by inappropriate levels or altered expression of functional Bia2 in a human or an animal using the anti-Bin2 antibody or diagnostic reagent of the invention. This method involves contacting an anti-Bin2 antibody or a diagnostic reagent containing same with a sample from a human or animal to be diagnosed, whereby in the presence of Bin2, a detectable complex is formed with the Bin2 protein or diagnostic reagent, analyzing for the presence or absence of said complex; and comparing the level of complex to a standard, wherein the absence of said detectable label indicates the absence of functional Bin2.

In still another aspect, the invention provides a kit for diagnosing a condition associated with Bin2 comprising a diagnostic reagent of the invention.

In a further aspect, the invention provides an anti-idiotype antibody specific for the anti-Bin2 antibody of the invention.

In yet another aspect, the invention provides a composition comprising an effective amount of a Bin2 protein or anti-idiotype of the invention and a pharmaceutically acceptable carrier.

In still another aspect, the invention provides a method of detecting inappropriate expression of Box dependent myc-interacting protein-2 (Bin2) in a patient comprising providing a sample from a patient suspected of having said inappropriate (over- or under-expression) or altered expression; incubating said sample in the presence of an anti-Bin2 antibody or a diagnostic reagent containing same; and comparing levels of expression to a normal Bin2 control.

In a further aspect, the invention provides a method of detecting inappropriate expression of Box-dependent myc-interacting peptide-2 Bin2) in a patient comprising providing a sample from a patent suspected of having said inappropriate expression and performing nucleic acid amplification using a Bin2 nucleic acid sequence of the invention.

In still a further aspect, the invention provides a method of identifying compounds which specifically bind to Bin2 or which specifically inhibit or block the binding of Bin2 to its ligand. In one embodiment, the method involves comprising the steps of contacting said Bin2 or a fragment thereof with a test compound to permit binding of the test compound to Bin2; and determining the amount of test compound which is bound to Bin2. In another embodiment, the invention provides a method of contacting an amount of immobilized first Bin peptide or a fragment thereof with a test compound and an amount of labeled second Bin peptide or fragment, wherein said first Bin peptide is either a Bin1 or a Bin2 peptide, and the second Bin peptide is the Bin peptide that binds said first Bin peptide. Unbound material is separated from immobilized material and the amount of label on said immobilized material is measured. A decrease in the amount of label immobilized in the presence of test compound compared to the amount of label immobilized in the presence of a control peptide or protein, indicates that said test compound inhibits the binding of Bin1 to Bin 2, or vice versa. The invention further provides a compound identified by this method.

Other aspects and advantages of the present invention are described further in the following detailed description of the preferred embodiments thereof.

BRIEF DESCRIPTION OF THE DRAWINGS

FIGS. 1A–1C illustrate the continuous sequence of full-length Bin2 cDNA [SEQ ID NO: 1] and the continuous amino acid sequence encoded thereby [SEQ ID NO: 2]. The initiating methionine codon is underlined and the stop codon TCT is indicated by an asterisk 5' and 3' noncoding sequences are shown.

FIG. 2 provides an alignment of the BAR domains of Bin2 [SEQ ID NO: 2] and Bin1 [SEQ ID NO: 3].

FIG. 4A provides the amino acid sequence alignment of Bin1 [SEQ ID NO: 3], Bin2 [SEQ ID NO: 2], and Daxn [SEQ ID NO: 4].

DETAILED DESCRIPTION OF THE INVENTION

Figure 3:
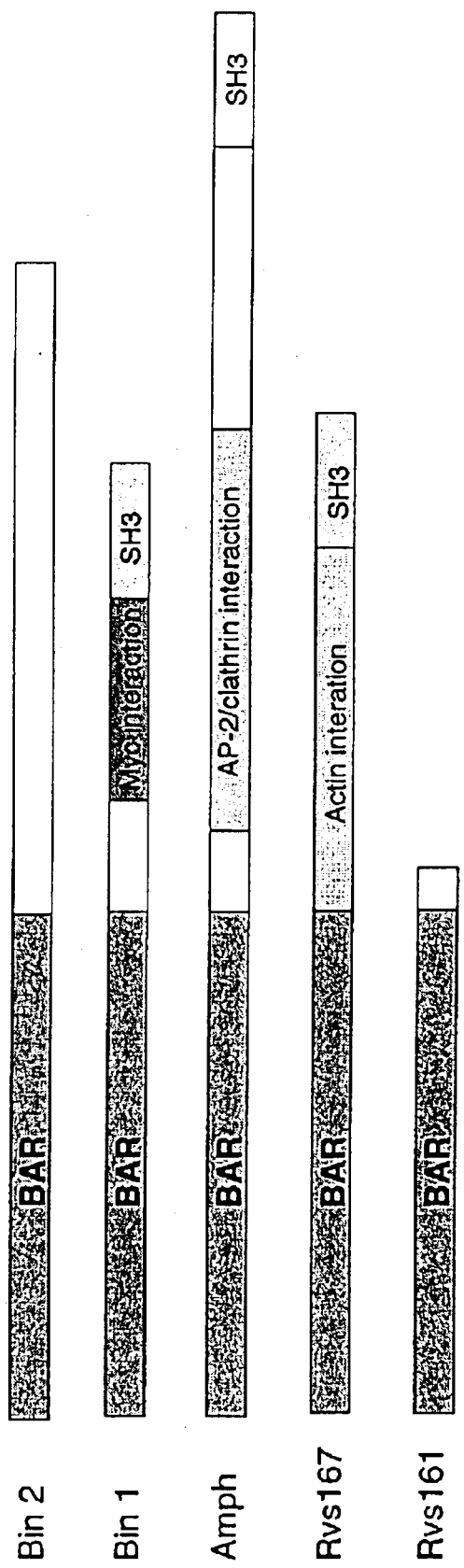
FIG. 3 is an illustration comparing Bin2 structure with other BAR family members.

The present invention provides novel, isolated mammalian Bin nucleic acid sequences, fragments thereof and proteins and peptides encoded thereby. The invention further provides methods of using these sequences, proteins, and compositions containing them for diagnosis and treatment of disorders associated with deregulation, deficiency or amplification of the c-myc oncogenes. The present invention further provides methods of using these sequences to generate antibodies and new compositions useful for such diagnosis and treatments.

The present invention provides Bin2 (Bridging INtegator-2), which is a novel member of the BAR family. Bin2 is expressed predominantly in hematopoietic cells and can form a stable complex with Bin1. Bin2 is upregulated during differentiation of granulocytes, thereby functioning in that cell lineage. Bin2 lacks sequences found in Bin1 that mediate c-Myc interaction. Bin2 also lacks sequences found in amphiphysin that mediate interaction with endocytotic machinery in the brain. In addition, Bin2 lacks a C-terminal region SH3 domain, instead including a C-terminal extension that is unrelated to other members of the BAR family. Database comparisons with Bin2 revealed a previously unrecognized region of similarity between BAR family proteins and Daxx, a nucleocytoplasmic adaptor implicated in programmed cell death, JNK signaling, and chromosomal regulation [Chang et al., Science 281: 1860–1863 (1998); Pluta et al., J. Cell Sci. 111: 2029–2041 (1998); Yang et al., Cell 89: 1067–1076 (1997)], within the central part of these proteins. The human Bin2 gene was mapped to chromosome 4q22.1, within a region that is frequently deleted in breast and liver cancers. However, unlike Bin1, which is ubiquitous and growth inhibitory, Bin2 was expressed predominantly in hemapoietic cells and was found to lack detectable antiproliferative activity. Thus, Bin2 is a novel BAR protein which has nonredundant functions relative to other members of the BAR family.

Compositions containing Bin2 proteins and nucleic acid sequences are useful for a variety of purposes. These aspects of the invention are discussed in more detail below.

I. Nucleic Acid Sequences

The present invention provides mammalian nucleic acid sequences encoding a Bin2 protein or peptide. The nucleic acid sequences of this invention may be isolated from cellular materials with which they are naturally associated or produced using techniques known in the art. In one embodiment, the present invention provides Bin2 nucleic acid sequence SEQ ID NO:1 and fragments of at least eight contiguous amino acids thereof. However, the present invention is not limited to these nucleic acid sequences.

Given the sequences of the Bin2 DNA [SEQ ID NO:1], one of skill in the art can readily obtain the corresponding anti-sense strands to these sequences. Further, using known techniques, one of skill in the art can readily obtain further sequences, including cDNA sequences or the corresponding RNA sequences, as desired.

Allelic variants of these sequences within a species (i.e., sequences containing some individual nucleotide differences from a more commonly occurring sequence within a species, but which nevertheless encode the same protein or a protein with the same function) may also be readily obtained given the knowledge of the nucleic acid sequence provided by this invention.

The present invention further encompasses nucleic acid sequences capable of hybridizing under stringent conditions [see, J. Sambrook et al, *Molecular Cloning A Laboratory Manual*, 2d ed., Cold Spring Harbor Laboratory (1989)] to the sequences of the invention, SEQ ID NO:1, their antisense strands, or biologically active fragments thereof. An example of a highly stringent hybridization condition is hybridization at 2×SSC at 65° C., followed by a washing in 0.1×SSC at 65° C. for an hour. Alternatively, an exemplary highly stringent hybridization condition is in 50% formamide, 4×SSC at 42° C. Moderately high stringency conditions may also prove useful, e.g. hybridization in 4×SSC at 55° C., followed by washing in 0.1×SSC at 37° C. for an hour. An alternative exemplary moderately high stringency hybridization condition is in 50% formamide, 4×SSC at 30° C.

According to the invention, the nucleic acid sequences may be modified. Utilizing the sequence data provided herein, it is within the skill of the art to obtain or prepare synthetically or recombinantly other polynucleotide sequences, or modified polynucleotide sequences, encoding the full-length proteins or useful fragments of the invention. Such modifications at the nucleic acid level include, for example, modifications to the nucleotide sequences which are silent or which change the amino acids, e.g. to improve expression or secretion. Also included are allelic variations, caused by the natural degeneracy of the genetic code.

Also encompassed by the present invention are nucleotide sequences encoding mutants of the Bin2 peptides and proteins provided herein. Such mutants include amino terminal, carboxy terminal or internal deletions, which substantially retain the biological activity (e.g., the antigenicity and/or the ability to bind Bin1) of the full-length Bin2 or other proteins or fragments. Such a truncated, or deletion mutant may be expressed for the purpose of affecting the activity of the full-length or wild-type gene or gene fragments.

Thus, the invention provides nucleic acid sequence fragments that encode a desirable fragment of Bin2, e.g., a Bin1 binding region. Generally, these oligonucleotide fragments are at least 15 nucleotides in length. However, oligonucleotide fragments of varying sizes may be selected as desired. Such fragments may be used for such purposes as performing polymerase chain reaction (PCR), e.g., on a biopsied tissue sample. For example, suitable nucleic acid fragments include those encoding the complete BAR motif or domain (amino acid 1 to 221 or amino acid 1 to 249 of SEQ ID NO:2) and the putative BAR effector region (amino acid 138–155 of SEQ ID NO:2). In one embodiment a fragment of this invention encodes at least 8 contiguous amino acids in length, e.g., a fragment selected from amino acids 1 to 13 of SEQ ID NO:2. In another embodiment, a nucleic acid sequence of this invention encodes at least 14 amino acids in length. Exemplary fragments include those encoding amino acids 23 to 35 or a peptide within amino acids 23 to 45 of SEQ ID NO:2. In still another embodiment, a nucleic acid sequence encodes a BIN2 fragment within amino acids 138–155 of SEQ ID NO:2 and comprises at least 19 amino acids in length. Still another nucleic acid sequence of the invention encodes a peptide of at least 8 amino acids in length within amino acids 179 to 336 of SEQ ID NO: 2. Still another nucleic acid sequence of the invention encodes a peptide of at least 8 amino acids in length within amino acids 250 to 564 of SEQ ID NO: 2, which is the region unrelated to the other BAR family proteins. In yet another embodiment, the nucleotide sequences of the invention encode analogs or homologs of SEQ ID NO:2. In still another embodiment, the nucleotide sequences of this invention encode fusion proteins comprising the amino acid sequence of SEQ ID NO: 2, a fragment, analog or homolog thereof, and a fusion partner. In still a further embodiment, a nucleotide sequence of this invention encodes a deletion protein comprising the amino acid sequence of SEQ ID NO:2 with one to twenty amino acids deleted therefrom. Other useful fragments may be readily identified by one of skill in the art by resort to conventional techniques.

The nucleotide sequences of the invention may be isolated by conventional uses of polymerase chain reaction or cloning techniques such as those described in obtaining the murine and human sequences, described below. Alternatively, these sequences may be constructed using conventional genetic engineering or chemical synthesis techniques.

These nucleic acid sequences are useful for a variety of diagnostic, prophylactic and therapeutic uses. Advantageously, the nucleic acid sequences are useful in the development of diagnostic probes and antisense probes for use in the detection and diagnosis of cancers and other conditions associated with inappropriate levels of functional Bin2 (and/or its binding partner, Bin1) or altered expression of Bin2 by utilizing a variety of known nucleic acid assays, e.g., Northern and Southern blots, polymerase chain reaction (PCR), and other assay techniques known to one of skill in the art. When used in diagnostic applications, the nucleic acid sequences of the invention may optionally be associated with a detectable label, such as are described in detail below. The nucleic acid sequences of this invention are also useful in the production of the peptides and proteins of the invention in vitro, in vivo, and ex vivo.

II. Protein Sequences

The present invention also provides mammalian Bin2 polypeptides or proteins. For convenience throughout this specification, reference will be made to "Bin2 peptides and proteins", but it will be understood that this tern encompasses the fragments, analogs, modified peptides and proteins, fusion proteins, and other amino acid constructs of the invention, except where otherwise specified.

These Bin2 peptides and proteins may be isolated in a form substantially free from other proteinaceous and non-proteinaceous cellular materials (e.g., hepatocytes) or from cell extracts. For example, these peptides and proteins may be isolated from the cellular materials and optionally, further purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatopraphy; gel electrophoresis, and the like. One of skill in the art may select the most appropriate isolation and purification techniques without departing from the scope of this invention.

Alternatively, the Bin2 peptides and proteins of the invention, described below, may be produced recombinantly following conventional genetic engineering techniques [see e.g., Sambrook et al, Molecular Cloning: A Laboratory Manual, Cold Spring Harbor Laboratories, Cold Spring Harbor, N.Y. and the detailed description of making the proteins below]. In still another alternative, the peptides and proteins of the invention may be produced using conventional chemical synthesis techniques, such as those described in G. Barony and R. B. Merrifield, The Peptides: Analysis, Synthesis & Biology, Academic Press, pp. 3–285 (1980), among others. The term "artificial" is used herein to denote the preparation of the construct (e.g., a peptide, protein, nucleic acid, or antibody of the invention) by chemical synthesis, recombinant technology, or other similar means.

The present invention further provides analogs, fragments, and mutant peptides, as well as proteins containing Bin2, or such analogs, fragments or mutants, as described below.

A. Analogs and Modified Peptide and Protein Antigens

Analogs or modified versions of the Bin2 proteins and peptides are provided. Typically, analogs differ from the specifically identified proteins by only one to four codon changes. Examples include polypeptides with minor amino acid variations from the illustrated amino acid sequence of Bin2 having conservative amino acid replacements. Conservative replacements are those that take place within a family of amino acids that are related in their side chains and chemical properties. Also provided are homologs of the proteins of the invention which are characterized by having at least 90% identity, and more preferably 95–99% identity with Bin2 sequences. Based on the sequence information provided herein, one of skill in the art can readily obtain full-length homologs and analogs.

As known in the art, "homology" or "identity" means the degree of sequence relatedness between two peptide or two nucleotide sequences as determined by the identity of the match between two lengths of such sequences. Both identity and homology can be readily calculated by methods extant in the prior art [See, e.g., COMPUTATIONAL MOLECULAR BIOLOGY, Lesk, A. M., ed., Oxford University Press, New York, (1988); BIOCOMPUTING: INFORMATICS AND GENOME PROJECTS, Smith, D. W., ed., Academic Press, New York, (1993); COMPUTER ANALYSIS OF SEQUENCE DATA, PART I, Griffin, A. M., and Griffin, H. G., eds., Humana Press, New Jersey, (1994); SEQUENCE ANALYSIS IN MOLECULAR BIOLOGY, von Heinje, G., Academic Press, (1987); and SEQUENCE ANALYSIS PRIMER, Gribskov, M. and Devereux, J., eds., M Stockton Press, New York, (1991)]. While there exist a number of methods to measure identity and homology between two nucleotide sequences, the terms "identity", "similarity" and "homolog" are well known to skilled artisans [H. Carillo and D. Lipton, *SIAM J. Applied Math.*, 48:1073 (1988)]. Methods commonly employed to determine identity or homology between two sequences include, but are not limited to, those disclosed in GUIDE TO HUGE COMPUTERS, Martin J. Bishop, ed., Academic Press, San Diego, 1994. Preferred methods to determine identity or homology are designed to give the largest match between the two sequences tested. Methods to determine identity and similarity are codified in computer programs. Preferred computer program methods to determine identity and homology between two sequences include, but are not limited to, the algorithm BESTFIT from the GCG program package [J. Devereux et al., *Nucl. Acids Res.*, 12(1):387 (1984)], the related MACVECTOR program (Oxford), and the FASTA (Pearson) programs, which may be used at default settings or modified settings such as determined to be suitable by one of skill in the art.

A Bin2 peptide or protein of the present invention may also be modified to increase its ability to bind and thus, complex with, Bin1. For example, the Bin2 peptide or protein may be coupled to chemical compounds or non-proteinaceous carriers. In certain embodiments, the coupling is designed not to interfere with the desired biological activity of either the Bin2 peptide or protein or the carrier. For a review of some general considerations in coupling strategies, see *Antibodies, A Laboratory Manual*, Cold Spring Harbor Laboratory, ed. E. Harlow and D. Lane (1988). For example, the carrier may be selected which facilitates cell penetration, e.g. a lipid or a carbohydrate. As another example, the carrier may be selected to deliver a toxin to Bin1, to which the Bin2 peptide binds. Such toxins are known to those of skill in the art and may include, e.g., chemical compounds including, without limitation, dinitrophenol groups and arsonilic acid. Yet other carriers may be selected simply to facilitate production or delivery of the Bin2 peptide or protein. For example, useful carriers known in the art, include, without limitation, keyhole limpet hemocyanin (KLH); bovine serum albumin (BSA), ovalbumin, agarose beads; activated carbon; or bentonite.

The Bin2 peptides and proteins of the invention may also be modified by other techniques, such as by denaturation with heat and/or SDS. Alternatively, the peptides and proteins of the invention may be modified to provide an additional N- or C-terminal amino acid sequence suitable for biotinylation, e.g., cysteine or lysine.

B. Fragments Deletion Mutants

Further encompassed by this invention are additional fragments of the Bin2 peptide or of the other proteins identified herein. Such fragments are desirably characterized by having a biological activity similar to that displayed by the complete protein, including, e.g., the ability to bind and complex with Bin1. These fragments may be designed or obtained in any desired length, including as small as about 5 to about 8 amino acids in length, about 14 or 15 amino acids in length, about 19 to 20 amino acids in length, or longer. Such a fragment represents less than the full-length Bin2 protein and may represent as little as a single epitope of the protein.

For example, one particularly desirable fragment of the invention is the BAR domain (amino acid 1 to 221 or amino acid 1 to 249 of SEQ ID NO:2), which contains dimerization signals. Optionally, one of skill in the art may utilize fragments with the BAR domain, which fragments are unique to BIN2, yet exhibit the desired biological function. Suitably, fragments of the BAR domain are composed of at least 14 amino acids in length with respect to any fragment which encompasses all of amino acids 1 to 13 or which encompasses all of amino acids 23 to 35 or amino acids 23 to 45 of SEQ ID NO:2. Another desirable fragment encompasses the putative BAR effector region (amino acid 138 to 155 of SEQ ID NO:2), which is implicated in Bin1 in tumor suppressor and programmed cell death signaling. Still other desirable fragments include fragments of about 8 or more amino acids from amino acids 250 to 564 of SEQ ID NO: 2, the C terminal region unrelated to other BAR family proteins. Suitably, any fragments of Bin2 containing these latter regions are at least 19 amino acids in length.

In yet another example, a Bin2 fragment may be a T cell epitope. Such a T cell epitope may be readily identified using available computer modeling programs.

Optionally, the peptides of the invention may be modified to create deletion mutants, for example, by truncation at the amino or carboxy termini, or by elimination of one or more amino acids. Still other modified fragments of Bin2 may be prepared by any number of now conventional techniques to improve production thereof, to enhance protein stability or other characteristics, e.g. binding activity or bioavailability, or to confer some other desired property upon the protein. Other useful fragments of these polypeptides may be readily prepared by one of skill in the art using known techniques, such as deletion mutagenesis and expression.

C. Fusion or Multimeric Proteins and Compositions

The Bin2 peptides and proteins of the present invention, or fragments of them, may also be constructed, using conventional genetic engineering techniques as part of a larger and/or multimeric protein or protein composition.

For example, such a fusion protein may be desirable in order to improve yield on expression and/or purification. Suitable fusion partners for such a purpose are well known to those of skill in the art and include, e.g., glutathione-S-transferase and maltose binding protein. Alternatively, a fusion protein of the invention may be composed of a Bin2 fragment, such as a fragment corresponding to a T cell epitope or to the Bin1 binding region, which is fused to an active agent.

The active agent may be composed of other Bin2 peptides and proteins of this invention, or may be other proteinaceous materials or nucleic acid molecule. For example, it may be desirable to fuse a Bin2 peptide or protein of the invention with a proteinaceous molecule which facilitates its cell penetration, e.g., *Drosophila antennapedia*, HIV Rev peptides, which are known to those of skill in the art. Alternatively, it may be desirable to fuse a Bin2 peptide or protein of the invention to a molecule which is to be targeted to a particular cell type and/orto Bin1. Particularly suitable are toxins and anti-cancer agents, any of which are known to those of skill in the an. However, suitable examples include, without limitation, tetanus toxoid, cholera toxoid, PPD (purified protein derivative of tuberculin), and molecular toxins such as imidazole protein cross-linkers or other conjugates (which would kill a bound Bin1 molecule). These proteins are effective in the prevention, treatment and diagnosis of cancers associated with inappropriate levels of functional Bin2 and/or inappropriate Bin1 function.

The fusion proteins of the invention are constructed for use in the methods and compositions of this invention. These fusion proteins may be produced recombinantly, or may be synthesized chemically. A protein composition which may be a preferred alternative to the fusion proteins described above is a cocktail (i.e., a simple mixture) containing a Bin2 peptide or protein, or different mixtures of the Bin2 peptides and proteins of this invention. In still another aspect, the peptide and proteins of the invention may be provided with a detectable label, such as are described in detail below.

D. Salts

A peptide or protein antigen of the present invention may also be used in the form of a pharmaceutically acceptable salt. Suitable acids and bases which are capable of forming salts with the polypeptides of the present invention are well known to those of skill in the art, and include inorganic and organic acids and bases.

III. Methods of Making Proteins and Nucleic Acid Sequences of the Invention Expression The proteins and nucleic acid molecules of the invention may be isolated from natural sources as described above, or may be produced using chemical synthesis techniques, such as are well known to those of skill in the art. In still another alternative, the peptides and proteins of the invention may be produced using conventional chemical synthesis techniques, such as those described in G. Barony and R. B. Merrifield, THE PEPTIDES: ANALYSIS, SYNTHESIS & BIOLOGY, Academic Press, pp. 3–285 (1980), among others. Particularly desirable, is the use of recombinant technology to produce the proteins and nucleic acid sequences of the invention.

A. Expression In Vitro

To produce recombinant Bin2 proteins of this invention, a DNA sequence of the invention is inserted into a suitable expression system. Desirably, a recombinant molecule or vector is constructed in which the polynucleotide sequence encoding Bin2 is operably linked to a heterologous expression control sequence permitting expression of the Bin2 protein. Numerous types of appropriate expression vectors are known in the art for protein expression, by standard molecular biology techniques. Such vectors may be selected from among conventional vector types including insects, e.g., plasmids, yeast, fungal, bacterial, insect (e.g., baculovirus expression) or viral expression systems. Other appropriate expression vectors, of which numerous types are known in the art, can also be used for this purpose. Methods for obtaining such expression vectors are well-known. See, Sambrook et al, MOLECULAR CLONING. A LABORATORY MANUAL, 2d edition, Cold Spring Harbor Laboratory, New York (1989); Miller et al, *Genetic Engineering*, 8:277–298 (Plenum Press 1986) and references cited therein.

Suitable host cells or cell lines for transfection by this method include mammalian cells, such as human 293 cells, Chinese hamster ovary cells (CHO), the monkey COS-1 cell line or murine 3T3 cells derived from Swiss, Balb-c or NIH mice may be used. Another suitable mammalian cell line is the CV-1 cell line. Still other suitable mammalian host cells, as well as methods for transfection, culture, amplification, screening, production, and purification are known in the an. [See, e.g., Gething and Sambrook, *Nature,* 293:620–625 (1981), or alternatively, Kaufman et al, *Mol. Cell. Biol.,* 5(7):1750–1759 (1985) or Howley of al, U.S. Pat. No. 4,419,446].

Similarly, bacterial cells are useful as host cells for the present invention. For example, the various strains of *E. coli* (e.g., FIB101, MC1061, and strains used in the following examples) are well-known as host cells in the field of biotechnology. Various strains of *B. subtilis*, Pseudomonas, other bacilli and the like may also be employed in this method. Many strains of yeast cells known to those skilled in the art are also available as host cells for expression of the polypeptides of the present invention. Other fungal cells may also be employed as expression systems. Alternatively, insect cells such as *Spodoptera frugipedera* (Sf9) cells may be used, e.g., in the baculovirus expression system. Alternatively, insect cells such as *Spodoptera frugipedera* (Sf9) cells may be used, e.g., in the baculovirus expression system.

Thus, the present invention provides a method for producing a recombinant Bin2 protein which involves transfecting a host cell with at least one expression vector containing a recombinant polynucleotide encoding a Bin2 protein under the control of a transcriptional regulatory sequence, e.g., by conventional means such as electroporation. The transfected host cell is then cultured under conditions that allow expression of the Bin2 protein. The expressed protein is then recovered, isolated, and optionally purified from the culture medium (or from the cell, if expressed intracellularly) by appropriate means known to one of skill in the art.

For example, the proteins may be isolated in soluble form following cell lysis, or may be extracted using known techniques, eg., in guanidine chloride. If desired, the Bin2 proteins of the invention may be produced as a fusion protein. For example, it may be desirable to produce Bin2 fusion proteins, to enhance expression of the protein in a selected host cell, to improve purification, or for use in monitoring the presence of Bin2 in cells, e.g., hepatocytes, or cell extracts. Suitable fusion partners for the Bin2 proteins of the invention are well known to those of skill in the art and include, among others, β-alactosidase, glutatliione-S-transferase, and poly-histidine.

B. Expression In Vivo

Alternatively, where it is desired that the Bin2 protein be expressed in vitao, e.g., for therapeutic purposes, an appropriate vector for delivery of Bin2, or fragment thereof, may be readily selected by one of skill in the art. Exemplary vectors are readily available from a variety of academic and commercial sources, and include, e.g., DNA vectors (including "naked" DNA and plasmid systems), adeno-associated virus, adenovirus vectors, or other viral vectors, e.g., various poxviruses, vaccinia, etc. Methods for insertion of a desired gene, e.g. Bin2, and obtaining in vivo expression of the encoded protein, are well known to those of skill in the art.

IV. Antibodies of the Invention

The Bin2 proteins of this invention are also useful as antigens for the development of anti-Bin2 antisera and antibodies to Bin2 or to a desired fragment of a Bin2 protein. Specific antisera may be generated using known techniques. See, Sambrook, cited above, Chapter 18, generally, incorporated by reference. Similarly, antibodies of the invention, both polyclonal and monoclonal, may be produced by conventional methods, including the Kohler and Milstein hybridoma technique and the many known modifications thereof. Similarly desirable antibodies are generated by applying known recombinant techniques to the monoclonal or polyclonal antibodies developed to these antigens [see, e.g., PCT Patent Application No. PCT/GB85/00392 British Patent Application Publication No. GB2188638A; Amit et al., Science, 233:747–753 (1986); Queen et at., Proc. Nat'l. Acad. Sci. USA, 86:10029–10033 (1989); PCT Patent Application No. PCT/WO9007861; and Riechmann et al. Nature, 332:323–327 (1988); Huse el a/, Science, 246:1275–1281 (1988)], or any other techniques known to the art.

Given the disclosure contained herein, one of skill in the art may generate chimeric, humanized or fully human antibodies directed against a Bin2 peptide or protein of the invention by resort to known techniques by manipulating the complementarity determining regions of animals or human antibodies to the Bin2 protein of the invention. See, e.g., E. Mark and Padlin, "Humanization of Monoclonal Antibodies", Chapter 4, THE HANDBOOK OF EXPERIMENTAL PHARMACOLOGY, Vol. 113, The Pharmacology of Monoclonal Antibodies, Springer-Verlag (June, 1994). Alternatively, the antigens may be assembled as multi-antigenic complexes [see, e.g., European Patent Application 0339695, published Nov. 2, 1989] or as simple mixtures of antigenic proteins/peptides and employed to elicit high titer antibodies capable of binding the selected antigen(s) as it appears in the biological fluids of an infected animal or human.

Further provided by the present invention are anti-idiotype antibodies (Ab2) and anti-anti-idiotype antibodies (Ab3). Ab2 are specific for the target to which anti-Bin2 antibodies of the invention bind and Ab3 are similar to Bin2 antibodies (Ab1) in their binding specificities and biological activities [see, e.g., M. Wettendorffet al., "Modulation of anti-tumor immunity by anti-idiotypic antibodies." In IDIOTYPIC NETWORK AND DISEASES, ed. by J. Cerny and J. Hiernaux J, Am. Soc. Microbiol., Washington D.C.: pp. 203–229, (1990)]. These anti-idiotype and anti-anti-idiotype antibodies may be produced using techniques well known to those of skill in the art. Such anti-idiotype antibodies (Ab2) can bear the internal image of Bin1 and bind to it in much the same manner as Bin2 and are thus useful for the same purposes as Bin2.

In general, polyclonal antisera, monoclonal antibodies and other antibodies which bind to Bin2 as the antigen (Ab1) are useful to identify epitopes of Bin2, to separate Bin2 from contaminants in living tissue (e.g., in chromatographic columns and the like), and in general as research tools and as starting material essential for the development of other types of antibodies described above. Anti-idiotype antibodies (Ab2) are useful for binding Bin2 and thus may be used in the treatment of cancers in which Bin2 is part of a biochemical cascade of events leading to carcinoma. The Ab3 antibodies may be useful for the same reason the Ab1 are useful. Other uses as research tools and as components for separation of Bin2 from other contaminants of living tissue, for example, are also contemplated for these antibodies.

For use in diagnostic assays, the antibodies are associated with conventional labels which are capable, alone or in concert with other compositions or compounds, of providing a detectable signal. Where more than one antibody is employed in a diagnostic method, the labels are desirably interactive to produce a detectable signal. Most desirably, the label is detectable visually, e.g. colorimetrically. A variety of enzyme systems have been described in the art which will operate to reveal a colorimetric signal in an assay. As one example, peroxidase, which reacts with peroxide and a hydrogen donor such as tetramethyl benzidine (TMB), produces an oxidized IMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength. Still another example is glucose oxidase (which uses glucose as a substrate) which releases peroxide as a product. Other label systems that may be utilized in the methods of this invention are detectable by other means, e.g., colored latex microparticles [Bangs Laboratories, Indiana] in which a dye is embedded may be used in place of enzymes to form conjugates with the antibodies and provide a visual signal indicative of the presence of the resulting complex in applicable assays. Still other labels include fluorescent compounds, radioactive compounds or elements. Detectable labels for attachment to antibodies useful in diagnostic assays of this invention may be easily selected from among numerous compositions known and readily available to one skilled in the art of diagnostic assays. The methods and antibodies of this invention are not limited by the particular detectable label or label system employed. Suitably, these detectable systems may also be utilized in connection with diagnostic reagents composed of the peptides, proteins, and nucleic acid sequences of the invention.

V. Diagnostic Reagents and Methods

Advantageously, the present invention provides reagents and methods useful in detecting and diagnosing a deficiency in normal Bin2 levels and/or abnormal levels of non-functional Bin2, and particularly deficiencies or excess production thereof, in a patient. Further, the present invention provides reagents which bind Bin1, and therefore as defined herein, a deficiency of Bin2 is an inadequate level of functional Bin2 to compensate for the levels of Bin1 in a patient. A deficiency of Bin1 is an inadequate level of functional Bin1 to compensate for the levels of c-Myc in a patient. Conditions associated with deficiencies of Bin2 include hepatocarcinoma; conditions associated with Bin1 include a variety of cancers, e.g., epithelial cell cancer, breast cancer, melanoma, prostate cancer, liver cancer and colon cancer, and hyperplastic disease states, e.g., benign prostate hyperplasia. Conditions associated with altered expression or loss of expression of normal Bin2 include myeloid and lymphoid leuklemias.

For convenience, reference will be made to Bin2 proteins throughout this and the following section. However, it will be understood that Bin2 nucleic acids (including anti-sense sequences and oligonucleotide fragments, among others), peptides, analogs and diagnostic compositions containing these molecules may be useful in these methods.

In one embodiment, this method involves detecting the presence of Bin1 (or other ligand for Bin2) which is produced by the affected human or animal patient's system and which are capable of binding to the Bin2 peptides and proteins (or Ab2) of this invention or combinations thereof. This method comprises the steps of incubating a Bin2 peptide or protein of this invention with a sample of biological fluids from the patient. Bin1 present in the samples will form a complex with the Bind peptide or protein. Subsequently the reaction mixture is analyzed to determine the presence or absence of these complexes. The step of analyzing the reaction mixture comprises contacting the reaction mixture with a labeled specific binding partner for the Bin2 ligand.

In one embodiment of the method, the Bin2 peptide or protein, or a mixture of the peptides and proteins of the invention is electro- or dot-blotted onto nitrocellulose paper. Subsequently, the biological fluid (e.g. serum or plasma) is incubated with the blotted peptide or protein, and ligand (e.g., Bin1) in the biological fluid is allowed to bind to the Bin2 peptide or protein. The bound ligand is then detected by standard immunoenzymatic methods.

In another embodiment of the method, latex beads are conjugated to the Bin2 peptide or protein of this invention. Subsequently, the biological fluid is incubated with the bead/protein conjugate, thereby forming a reaction mixture. The reaction mixture is then analyzed to determine the presence of Bin1 or other Bin2 ligand.

In another embodiment, the diagnostic method of the invention involves detecting the presence of the naturally occurring Bin2 peptide or protein itself in its association with hepatocytes in the biological fluids of an animal or human infected by the pathogen. This method includes the steps of incubating a ligand specific for Bin2 (e.g., Bin1 or an antibody of this invention, e.g. produced by administering to a suitable human and/or animal an antigen of this invention), preferably conventionally labelled for detection, with a sample of biological fluids from a human or an animal to be diagnosed. In the presence of Bin2, a complex is formed (specific binding occurs). Subsequently, excess labeled antibody (or other ligand) is optionally removed, and the reaction mixture is analyzed to determine the presence or absence of the antigen-antibody complex and the amount of label associated therewith.

Assays employing a peptide or protein of the invention can be heterogenous (i.e., requiring a separation step) or homogenous. If the assay is heterogenous, a variety of separation means can be employed, including centrifugation, filtration, chromatography, or magnetism.

One preferred assay for the screening of blood products or other physiological or biological fluids is an enzyme linked immunosorbant assay, i.e., an ELISA. Typically in an ELISA, the isolated Bin2 peptide or protein of the invention is adsorbed to the surface of a microtiter well directly or through a capture matrix (i.e., antibody). Residual protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing Bin1 or another ligand specific for Bin2. The sample can be applied neat, or more often, it can be diluted, usually in a buffered solution which contains a small amount (0.1–5.0% by weight) of protein, such as BSA, NGS, or BLOTTO. After incubating for a sufficient length of time to allow specific binding to occur, the well is washed to remove unbound protein and then incubated with labeled anti-human immunoglobulin (a HuIg) or labeled antibodies to other species, e.g., dogs. The label can be chosen from a variety of enzymes, including horseradish peroxidase (HRP), β-galactosidase, alkaline phosphatase, and glucose oxidase, as described above. Sufficient time is allowed for specific binding to occur again, then the well is washed again to remove unbound conjugate, and the substrate for the enzyme is added. Color is allowed to develop and the optical density of the contents of the well is determined visually or instrumentally.

Further, MAbs or other antibodies of this invention which are capable of binding to Bin2 peptides and proteins can be bound to ELISA plates. In another diagnostic method, the biological fluid is incubated on the antibody-bound plate and washed. Detection of any antigen-antibody complex, and qualitative measurement of the labeled MAb is performed conventionally, as described above.

Other useful assay formats include the filter cup and dipstick. In the former assay, an antibody of this invention is fixed to a sintered glass filter to the opening of a small cap. The biological fluid or sample (5 mL) is worked through the filter. If Bin1 is present, it will bind to the filter which is then visualized through a second Bin2 peptide or protein. The dipstick assay involves fixing an antigen or antibody to a filter, which is then dipped in the biological fluid, dried and screened with a detector molecule.

Other diagnostic assays can employ the antigen(s) or fragments of this invention as nucleic acid probes or as anti-sense sequences, which can identify the presence of infection in the biological fluid by hybridizing to complementary sequences produced by the pathogen in the biological fluids. Such techniques, such as PCR, Northern or Southern hybridizations etc. are well known in the art.

It should be understood by one of skill in the art that any number of conventional protein assay formats, particularly immunoassay formats, or nucleic acid assay formats, may be designed to utilize the isolated antigens and antibodies or their nucleic acid sequences or anti-sense sequences of this invention for the detection of disorders associated with inappropriate/altered levels of functional Bin and/or for monitoring inappropriate levels of Bin1 in animals and humans. This invention is thus not limited by the selection of the particular assay format, and is believed to encompass assay formats which are known to those of skill in the art.

VI. Diagnostic Kits

For convenience, reagents for ELISA or other assays according to this invention may be provided in the form of kits. Such kits are useful for diagnosing conditions associated with dysfunctional Bin2 levels and/or Bin1 levels, including cancers in a human or an animal sample. Such a diagnostic kit contains an antigen of this invention and/or at least one antibody capable of binding an antigen of this invention, or the nucleic acid sequences encoding them, or their anti-sense sequences.

Alternatively, such kits may contain a simple mixture of such antigens or sequences, or means for preparing a simple mixture.

These kits can include microtiter plates to which the Bin2 peptides, proteins, antibodies, or nucleic acid sequences of the invention have been pre-adsorbed, various diluents and buffers, labeled conjugates for the detection of specifically bound antigens or antibodies, or nucleic acids and other signal-generating reagents, such as enzyme substrates, cofactors and chromogens. Other components of these kits can easily be determined by one of skill in the art. Such components may include polyclonal or monoclonal capture antibodies, antigen of this invention, or a cocktail of two or more of the antibodies, purified or semi-purified extracts of these antigens as standards, MAb detector antibodies, an anti-mouse or anti-human antibody with indicator molecule conjugated thereto, an ELISA plate prepared for absorption, indicator charts for colorimetric comparisons, disposable gloves, decontamination instructions, applicator sticks or containers, and a sample preparator cup. Such kits provide a convenient, efficient way for a clinical laboratory to diagnose Bin2-associated conditions.

VII. Therapeutic Compositions and Methods

Compositions and methods useful for the treatment of conditions associated with inappropriate Bin2 levels are provided. Bin2 is expressed predominantly in blood, e.g., hematopoietic, cells and is upregulated during monocytic differentiation. Thus, Bin2 levels have been detected in spleen and peripheral blood leukocytes, and in thymus, colon and placenta, and Bin2 RNA has been strongly expressed in several human lymphoid and Lymphoid cell lines, including GM1500, ALL200, BVV173 and HL60. Bin2 was induced during granulocytic differentiation of HL60 cells, a promyelocytic leukemia cell line. Included among conditions related to Bin2 expression include disorders associated with blood cells and hepatocytes, including hepatocarcinomas and certain myeloid or lymphoid leukemias. Further, Bin2 may be useful in directing treatment to disorders associated with inappropriate Bin1 functions, and particularly, for inhibiting excessive Bin1 levels. These Bin1-associated disorders include liver, colorectal, prostate, and breast cancers, epithelial cell cancers, melanoma, and hyperplastic disease states.

The therapeutic compositions of the invention may be formulated to contain an anti-idiotype antibody of the invention, the Bin2 protein itself or a fragment thereof, or nucleic acid sequences which direct expression of these antibodies, proteins or fragments thereof, including anti-sense sequences. The therapeutic composition desirably contains 0.01 $\mu$g to 10 mg protein. These compositions may contain a pharmaceutically acceptable carrier, which facilitate administration of the compositions but are physiologically inert and/or nonharmful. Suitable carriers are well known to those of skill in the art and include, for example, saline. Alternatively, such compositions may include conventional delivery systems into which protein of the invention is incorporated. Optionally, these compositions may contain other active ingredients, e.g., chemotherapeutics.

Carriers may be selected by one of skill in the art. Exemplary carriers include sterile saline, lactose, sucrose, calcium phosphate, gelatin, dextran, agar, pectin, peanut oil, olive oil, sesame oil, and water. Additionally, the carrier or diluent may include a time delay material, such as glycerol monostearate or glycerol distcarate alone or with a wax. In addition, slow release polymer formulations can be used.

Optionally, this composition may also contain conventional pharmaceutical ingredients, such as preservatives, or chemical stabilizers. Suitable ingredients which may be used in a therapeutic composition in conjunction with the antibodies include, for example, casamino acids, sucrose, gelatin, phenol red, N-Z amine, monopotassium diphosphate, lactose, lactalbumin hydrolysate, and dried milk.

Alternatively, or in addition to the antibodies of the invention, other agents useful in treating hepalocarcinoma or other conditions associated with dysfunctional Bin2 levels, are expected to be useful in reducing or eliminating disease symptoms.

Such agents may operate in concert with the therapeutic compositions of this invention. The development of therapeutic compositions containing these agents is within the skill of one in the art in view of the teachings of this invention.

According to the method of the invention, a human or an animal may be treated for hepatocarcinoma by administering an effective amount of such a therapeutic composition. An "effective amount" may be between about 0.05 to about 1000 $\mu$g/mL of a Bin2 peptide, protein or antibody of the invention. A suitable dosage may be about 1.0 mL of such an effective amount. Such a composition may be administered 1–3 times per day over a 1 day to 12 week period. However, suitable dosage adjustments may be made by the attending physician or veterinarian depending upon the age, sex, weight and general health of the human or animal patient. Preferably, such a composition is administered parenterally, preferably intramuscularly or subcutaneously. However, it may also be formulated to be administered by any other suitable route, including orally or topically.

Still another composition contains Bin2 polynucleotide sequences which contain regulatory sequences which regulate expression of the proteins of the invention in vivo or in vitro. Generally, a DNA-based composition contains 0.05 $\mu$g to 1 mg DNA per mL dose. Where the antigen-encoding polynucleotide sequences are carried on a viral vector, a dose may be in the range of $1\times10^{-3}$ pfu to $1\times10^{13}$ pfu per dose. However, the dose, timing and mode of administration of these compositions may be determined by one of skill in the art. Such factors as the age, condition, and the level of the Bin2 deficiency detected by the diagnostic methods described above, may be taken into account in determining the dose, timing and mode of administration of the therapeutic compositions of the invention. Generally, where treatment of an existing cancer or hyperplastic state is indicated, a therapeutic composition of the invention is preferably administered in a site-directed manner and is repeated as needed. Such therapy may be administered in conjunction with conventional therapies, including radiation and/or chemotherapeutic treatments.

VIII. Drug Screening and Development

The Bin2 peptides, antibodies and polynucleotide sequences of the present invention are also useful in the screening and development of chemical compounds or proteins which have utility as therapeutic drugs for the treatment of cancers associated with inappropriate Bin2 levels.

Suitable assay methods may be readily determined by one of skill in the art. Where desired, and depending upon the assay selected, Bin2 may be immobilized directly or indirectly (e.g., via an anti-Bin2 antibody) on a suitable surface, e.g., in an ELISA format. Such immobilization surfaces are well known. For example, a wettable inert bead may be used. Alternatively, Bin2 may be used in screening assays which do not require immobilization, e.g., in the screening of combinatorial libraries. Assays and techniques exist for the screening and development of drugs capable of binding to selected regions of Bin2. These include the use of a phage display system for expressing the Bin2 proteins, and using a culture of transfected *E. coli* or other microorganism to produce the proteins for binding studies of potential binding compounds. See, for example, the techniques described in G. Cesarini, FEBS Letters, 307(1):66–70 (July 1992); H. Gram et al, *J. Immunol. Meth.*, 161:169–176 (1993); C. Summer et al., *Proc. Natl. Acad. Sci. USA*, 89:3756–3760 (May 1992).

Other conventional drug screening techniques may be employed using the Bin2 peptides, antibodies or polynucleotides of this invention. As one example, a method for identifying compounds which specifically bind to a Bin2 protein can include simply the steps of contacting a selected Bin2 protein with a test compound to permit binding of the test compound to the Bin2 protein; and determining the amount of test compound, if any, which is bound to the Bin2 protein. Such a method may involve the incubation of the test compound and the Bin2 protein immobilized on a solid support.

Typically, a surface containing the immobilized ligand is permitted to come into contact with a solution containing the Bin2 protein and binding is measured using an appropriate detection system. Suitable detection systems include, without limitation, the streptavidin horseradish peroxidase conjugate and direct conjugation by a tag, e.g, fluorescein. Other systems are well known to those of skill in the art. This invention is not limited by the detection system used.

Another method of identifying compounds which specifically bind to a Bin2 protein can include the steps of contacting a Bin2 protein immobilized on a solid support with both a test compound and the protein sequence which is a receptor for Bin2 to permit binding of the receptor to the Bin2 protein; and determining the amount of the receptor which is bound to the Bin2 protein. The inhibition of binding of the normal protein by the test compound thereby indicates binding of the test compound to the Bin2 protein.

In still another method, interaction blockers may be identified. As an example a simple plate assay could be used to screen for such blockers. In one embodiment of a plate assay one peptide/protein is bound to the dish and the other is added in an aqueous buffer (physiological KCl, e.g. 150 mM, and pH, eg. 7.5). Binding is monitored using an antibody to the peptide which is conjugated to a fluorescent or enzymological marker (e.g., fluorescein or HRP). The primary antibody could also be detected by using an anti-primary antibody that is so tagged. The binding conditions are empirically optimized for salt, pH, metal, and detergent conditions. Under optimized binding conditions, the assay is run in such a fashion that peptides or peptidomimetic drugs are added to the binding buffer. The positive control for blocking binding is provided by addition of excess Bin protein, whereas the negative control is an unrelated protein or scrambled peptide. For example, a GST-Bin1 protein is used to coat a plate and a Bin2 peptide used for binding. The peptide is directly identified by an antibody; alternatively, it is epitope tagged. Still alternately, the peptide itself is conjugated to the marker desired. This type of assay is amenable to high throughput screening since it can be configured in a 96-well format.

Thus, through use of such methods, the present invention provides compounds capable of interacting with Bin2, or selected portions thereof, and either enhancing or inhibiting its biological activity, as desired. The assay methods described herein are also useful in screening for inhibition of Bin2. The solution containing the inhibitors may be obtained from any appropriate source, including, for example, extracts of supernatants from cultures of bioorganisms, extracts from organisms collected from natural sources, chemical compounds, and mixtures thereof.

The following examples illustrate the isolation and use of the Bin1 sequences of the invention. These examples are illustrative only and do not limit the scope of the invention.

EXAMPLE 1

BIN2 is a Novel Bar Family Adaptor Protein that Lacks an SH3 Domain

An anti-Bin1 polyclonal antisera was previously observed to crossreact with Bin1-related polypeptides in cells [Sakamuro et al, *Nature Genet.* 14: 69–77 (1996)), suggesting that additional uncharacterized members of the BAR family existed in mammalian cells. Subsequent epitope mapping of the main regions of Bin1 recognized by this antisera defined a major epitope between the extreme C-terminus of the BAR domain [Wechsler-Reya et al., *Cancer Res.* 57: 3258–3263 (1997)]. A TBLASTN search of the expressed sequence tag (EST) database with the amino acid sequence containing this epitope identified a germinal B cell cDNA (Genbank accession number AA452680) which encoded a polypeptide related to but nonidentical to amphiphysin or Bin1. Using this EST cDNA as a probe a full-length cDNA was obtained from a human leukocyte phage library and its complete DNA sequence was determined using standard methods [see, e.g., Sambrook et al, cited above]. A long open reading frame (ORF) identified in this cDNA encoded a 564 amino acid polypeptide rich in serine and glutamic acid with a predicted molecular weight of 61,709 Da (see FIGS. 1A–1C). Using the BLAST2 algorithm to compare Bin1 with this polypeptide, termed Bin2 (Bridging INtegrator-2), the presence of a complete BAR motif that had 61% identity and 75% similarity with boundaries of amino acid 1–249 of Bin2 and amino acid 1–251 of Bin1 (see FIG. 2) was confirmed. In particular. Bin2 was identical to Bin1 within a region of the latter (amino acid 138–155) which is most highly conserved region in BAR family proteins in evolution (G.C.P., unpublished observations), whereas amphiphysin has a nonidentical residue in this region and was slightly less similar overall (data not shown). Bin2 lacked any canonical motifs other than the BAR domain (see FIG. 3). In particular, it lacked an S1H3 domain which is found at the C-terminus of Bin1, amphiphysin, and RVS167. While RVS161 also lacks an SH3 domain, Bin2 differs in that it includes a large C-terminus that extends beyond the BAR domain. Notably, Bin2 lacked sequences implicated in normeuronal isoforms of Bin1 in interaction with c-Myc or TATA-binding protein in the nucleus (Sakamuro et al. cited above] or in alternately spliced neuronal isoforms in interaction with clathrin [Ramjaun and McPherson, J. Neurochem. 70: 2369–2376 (1998)] or AP-2 (P. de Camilli, pers. comm.). Thus, the structure of Bin2 suggested strongly that it represented a nonredundant function. Southern analysis confirmed the presence of Bin2 sequences in human genomic DNA (see below). It was concluded that Bin2 was a novel mammalian member of the BAR family of adaptor proteins.

EXAMPLE 2

The Human BIN2 Gene is Located on Chromosome 4q221 and Exhibits Aberrant Organization in Hepatoma Cells The Bin2 cDNA was used to isolate three human Bin2 genomic BAC clones by standard methods. Restriction analysis and Southern hybridization of these clones and comparison to Genomic Southern hybridizations confirmed the presence of Bin2 sequences and ruled out the possibility that a pseudoene was cloned. One of the clones, F727, was used to perform fluorescence in situ hybridization (FISH) analysis of metaphase chromosomes isolated from normal peripheral blood lymphocytes, essentially as described in *Cells: A Laboratory Manual*, vol. 3, p. 111.1–111.44, D. L. Spector et al, eds., Cold Spring Harbor Press, Cold Spring Harbor N.Y. 1998.

More particularly, fluorescence in situ hybridization (FISH) was performed using a Bin2 genomic BAC clone labeled by nick translation with digoxigenin dUTP and metaphase chromosomes isolated from PHA-stimulated normal peripheral blood lymphocytes. A biotin-labelled probe specific for the centromere of chromosome 4 was prepared and also included in the hybridization. Slides were developed using a fluoresceinated anti-digoxigenin antibodies and Texas red avidin.

Specific hybridization signals were detected on the long arm of a group B chromosome consistent with chromosome 4 on the basis of size, morphology, and banding pattern. An experiment which included a second probe specific for the centromere sequences of chromosome 4 confirmed this interpretation. A total of 80 metaphase cells analyzed with 73 exhibiting specific labeling. Measurements of 10 specifically labeled chromosomes 4 demonstrated that the Bin2-specific hybridization signal was located at a position 27% the distance from the centromere to the telomere of chromosome arm 4q, an area corresponding to band 4q22.1. Two studies have reported this region to be deleted in>50% of breast carcinomas [Schwendel et al., Br. *J. Cancer* 78: 806–811 (1998)], with an even higher frequency in tumors harboring BRCA1 mutations [Tirkkonen et al., *Cancer Res.* 57: 1222–1227 (1997)], and a third study has reported this region to be deleted in>75% of hepatocarinomas [Yeh et al, *Gastroenterology* 110: 184–192 (1996)]. The structure of the Bin2 gene in normal human foreskin, HepG2 or HLF hepatoma cells, and DU 145 prostate carcinoma cells was compared by genomic Southern analysis to assess the possibility of structural alteration.

For the Southern analysis, genomic DNA isolated from human foreskin, HepG2 or HLF hepatoma cells, or DU145 prostate carcinoma cells (as a negative control) was analyzed by standard Southern analysis using the Bin2 cDNA as a hybridization probe. Both HepG2 and HLF exhibited normal and aberrant banding patterns relative to normal foreskin and DU145 cells, which showed the same pattern as foreskin, consistent with alteration of at least one allele of the Bin2 gene in certain liver tumors. Similar to DU145, genomic DNAs isolated from a panel of nonmalignant and malignant B lymphoid cell lines (Daudi, Raji, 380, GM1500, G97, BVI 73) also did not exhibit aberrant organization of the Bin2 gene. It was concluded that the Bin2 gene localized to chromosome 4q22.1 within a region that was altered in hepatocellular tumors.

EXAMPLE 3

Evidence of Similarity Between BIN2, BIN1, and DAXX

Figure 4B:
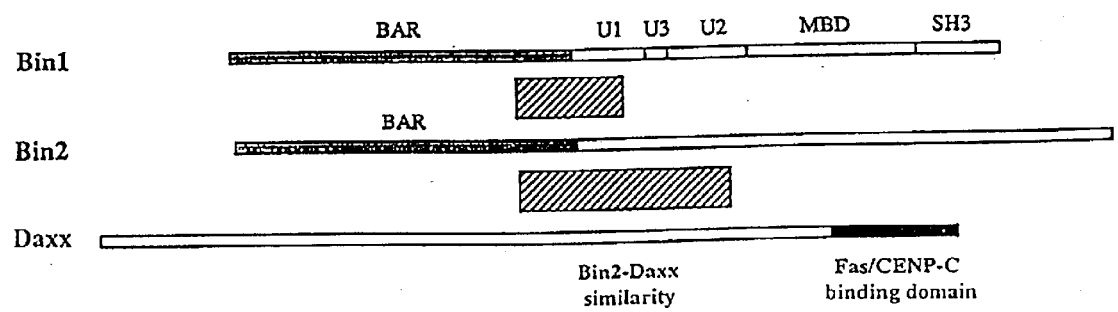
FIG. 4B is an illustration of the domains in Bin1, Bin2, and Daxx and the relative region of similarity between Bin2 and Daxx (dark shaded).

In an effort to gain insight into the function of Bin2, the sequences in its central and C-terminal regions were compared to the DNA database using the BLAST algorithm. Searches conducted with sequences derived from the central region of Bin2, including a C-terminal part of the BAR domain, revealed a region (amino acid 179–336) that was similar to a functionally undefined central region of Daxx, an adaptor protein implicated in Jun kinase (JNK) signaling and interactions with the programmed cell death receptor CD95/Fas in the cytosol and the centromere-binding protein CENP-C in the nucleus [Chang et al, *Science* 281: 1860–1863 (1998); Pluta et al. *J. Cell Sci.* 111:2029–2041 (1998); Yang et al. Cell 89: 1067–1076 (1997); Zhang et al., *Nature* 392: 296300 (1998)]. The alignment included part of the BAR domain and Bin1 and amphiphysin could also be aligned with Daxx. Table I illustrates the similarity between central regions of Bin2 and Daxx. Amino acid sequences from the central region of Bin2 were used to query the DNA database for related sequences using the TBLASTN algorithm. This figure provides the selected hits and significance scores. The query sequence was amino acid 179–336 in Bin) [SEQ ID NO: 2]. The score for the Daxx hit was more significant than the hit to the related yeast BAR protein RVS161 (underlined). See, also, FIGS. 4A and 4B.

TABLE 1

| Sequences producing significant alignments | Score (bits) | E Value |
| --- | --- | --- |
| gi 1438562 gb U60884 MMU60884 *Mus musculus* SH3P9 mRNA, complete . . . | 117 | 1e-25 |
| gi 550449 gb U07616 HSU07616 Human amphiphysin mRNA, complete cds. | 113 | 1e-24 |
| gi 2199534 gb AF001383 AF001383 *Homo sapiens* amphiphysin II mRNA . . . | 113 | 2e-24 |
| gi 1710134 gb U68485 HSU68485 Human Box-dependent MYC-interacti . . . | 111 | 7e-24 |
| gi 2323471 gb AF015956 AF015956 *Homo sapiens* Fas-binding protein . . . | 41 | 0.009 |
| gi 976346 gb L32832 HUMZFHP *Homo sapiens* zinc finger homeodomai . . . | 40 | 0.020 |
| gi 2745970 gb U84003 HSTSBIN5 *Homo sapiens* putative tumor suppr . . . | 39 | 0.058 |
| gi 1122811 emb Z68217 CEF58G6 *Caenorhabditis elegans* cosmid F58 . . . | 38 | 0.076 |
| gi 4417 emb X63315 SCRVS161 *S. cerevisiae* RVS 161 gene | 38 | 0.076 |
| gi 4057 emb X57185 SCNSR1 Yeast NSR1 gene for nuclear localizat . . . | 37 | 0.22 |
| gi 29860 emb X55039 HSCENPB Human hCENP-B gene for centromere a . . . | 36 | 0.29 |

However, whereas the extent and significance of the alignments to Bin1 and amphiphysin were relatively lower, the E value computed by BLAST for the Bin2-Daxx alignment ranked it stronger than that the analogous alignment between Bin2 and the yeast BAR family member RVS 161 (9e-3 versus 7.6e-2, respectively). The rank related in part to a shared glutamate-rich segment found in Bin2 and Daxx but absent from other BAR family members. It was concluded that Bin2 and Daxx shared a similar region of structure within a central region of each polypeptide.

The database comparisons identified a region of similarity between the central domains of Bin2 and Daxx, a nucleo-cytosolic adaptor protein linked to cell survival decisions and chromosome function. The functional implications of this relationship are unclear. Daxx was initially identified through its ability to interact with the death domain of CD95/Fas, a member of the tumor necrosis factor (TNF) superfamily of cell surface death receptors. Initial investigations suggested a role for Daxx in death signaling by CD95/Fas [Yang et al. 1997, cited above], but more recent studies have suggested that while Daxx may have a role in JNK signaling by the receptor it is dispensable for death signaling [Chang et al., Science 281: 1860–1863 (I 998); Chang et al., Proc. Natl. Acad. Sci. USA 96: 1252–1256 (1999)]. Another study identified Daxx through its ability to interact with CENP-C, a centromere-binding protein. While the meaning of this interaction is not yet known, consistent with some nuclear role Daxx has also been found to interact with the cancer-related protein Pm1 and to localize to the subnuclear domain ND10 where Pm1 can be found (G. Maul, pers. comm.). Interestingly, Pm1 and Bin1 have each been demonstrated to have a role in certain types of programmed cell death [Quignonce at. Nat. Genet. 20: 259–265 (1998); Wang et al., Nat. Genet. 20: 266–272 (1998)]. Therefore, it is tempting to speculate that the relationship between Daxx and Bin2 may reflect some related connection to cell survival controls. This possibility would be consistent with the apparent role of RVS proteins in yeast survival, following stresses which result from nutrient starvation.

EXAMPLE 4

BIN2 is Expressed Predominantly in Hematopoietic Cells and is Upregulated During Monocytic Differentiation Northern analyses of total RNAs isolated from human tissues and cell lines were performed using the Bin2 cDNA as a hybridization probe to investigate the range of expression of Bin2 and to compare it with amphiphysin and Bin1 expression. Prior to Northern analysis, cells were treated with DMSO or RA for 1, 3 or 5 days and RNA was isolated for Northern analysis with Bin2 cDNA. The human tissues studied included heart, brain, placenta, lung, liver, skeletal muscle, kidney, pancreas, spleen, thymus, prostate, testis, ovary, small intestine, colon, and peripheral blood leukocytes. The cell lines included: Raji, 380, 697, VM173, GM1500, ALL200, Daudi, HepG2, Caco-2, HCT116, LoVo, HBL100, ZR75-1, MCF7, BT20, SK-BR-3, A549, HLF, DU145, LNCaP, PC3, U373, U87-MG, and NCH2. Also determined was the level of Bin2 induction during differentiation of HL60 promyelocytic leukemia cells to monocytes.

Northern hybridization of human tissue blots obtained from Clontech initially suggested a broad range of expression, similar to Bin1 and in contrast to amphiphysin (results not shown). Two Bin2 messages were noted in most tissues, suggesting alternate splicing as occurs in Bin1 [Wechsler-Reya et al., J. Biol. Chem. 272: 31453–31458 (1997)]. The highest levels of Bin2 message were seen in spleen, peripheral blood leukocytes, thymus, placenta, testis, colon, liver, and lung. The pattern of expression more resembled Bin 1, which is ubiquitous but expressed at highest levels in skeletal muscle, than amphiphysin, which is essentially specific to the central nervous system. However, additional experiments suggested that Bin2 might be preferentially expressed in hemapoietic cells and that the apparent pattern of ubiquitous expression reflected contamination of various tissues with hematopoietic cells, where Bin2 was expressed at high levels. For example, Bin2 message was barely detectable or undetectable by Northern analysis in 21 human cell lines derived from a variety of tissues, including breast, lung, prostate, brain, connective tissue (fibroblast), liver, and colon, despite the detection of Bin2 in these tissues. In contrast, Bin2 message was strongly expressed in several lymphoid cell lines (GM1500, ALL200, BV173, Jurkat) and in myeloid cells (HL60) that are derived from the hematopoictic lineage. Given that the Bin2 gene may be altered in the cell lines examined, which were immortalized or malignant, it was possible that the inability to detect expression was due to functional loss. The likelihood that Bin2 was predominantly expressed in hematopoietic cells was supported by "virtual" Northern analyses, performed by comparing Bin2 sequences to the EST database, which provides information about the source of the cDNA. The majority of identical ESTs identified in this manner bad been cloned from cDNA libraries derived from germinal B lymphoid cells, fetal liver (which is rich in B lymphoid cells), and placenta (which is rich in myeloid cells), although kidney libraries were also represented. One cell line identified to be positive for Bin2 expression was HL60 promyclocytic leukemia cells, which can be induced to differentiate to monocytes by treatment with dimethyl sulfoxide (DMSO) or to granulocytes by treatment with retinoic acid (RA). To assess the possibility that Bin2 may function in differentiated myeloid cells, it was determined whether the level of Bin2 message was altered during HL60 differentiation down the monocytic or granulocytic pathways. Northern analysis demonstrated that Bin2 levels were increased within 5 days of DMSO but not RA treatment. The level of Bin2 following induction was similar to that found in human U937 myeloid cells and higher than in Jurkat T lymphoid cells. The elevation of Bin2 during differentiation was reminiscent of a similar elevation of Bin1 which occurs during differentiation of skeletal myoblasts and certain other cells including smooth muscle and keratinocytes [Mao et al., Genomics 56: 51–58 (1999); Wechsler-Reya et al. Mol. Cell. Biol. 18: 566–575 (1998)]. It was concluded that Bin2 was expressed predominantly in hematopoietic cells and was likely to function in the myeloid lineage.

Bin2 is expressed predominantly in hemapoietic cells. This pattern of expression contrasts with amphiphysin, which is largely restricted to the central nervous system, as well as with Bin1, which is highly expressed in muscle but otherwise ubiquitous. Induction of Bin2 message was documented in a model system for monocytic differentiation, in support of the notion that Bin2 is likely to have an important function(s) in the hematopoietic lineage. Whether the Bin2 gene has important functions in other tissues is not yet clear. While expression was documented by Northern analysis in many normal tissues, these results could be ascribed to contamination of tissues with hemapoietic cells: while Bin2 message was abundant in lymphoid and myeloid cells, it was undetectable in most benign and malignant non-hemapoietic cell lines examined. It is conceivable that some of the deficits seen may be due to losses in malignant settings, such as is the case with Bin1 [Sakamuro et al., Nature Genet. 14: 69–77 (1996)]. Consistent with this possibility, the Bin2 gene is located at chromosome 4q22.1, a region frequently disrupted in hepatocarcinoma, and aberrant organization of the gene was observed in two liver tumor lines. Bin2 was not expressed in these lines but little effect of ectopic Bin2 on the proliferation of these cell lines in vitro was noted, so the significance of the aberrant gene organization and possible loss of expression remains unclear.

EXAMPLE 5

BIN2 and BIN1 Form a Stable Complex That Requires the Bar Domain

Stable complexes have been reported in yeast between RVS161 and RVS167 and in brain between amphiphysin and brain-specific splice isoforms of Bin1 [Navarro et al., *Biochim. Biophys. Acta.* 1343: 187–192 (1997); Wigge et al., *Mol. Biol. Cell* 8: 2003–2015 (1997)]. Since Bin1 is expressed in hematopoietic cells, whether Bin2 and Bin1 could also form a stable biochemical complex was investigated. For communoprecipitation experiments, Bin1 was in vitro translated in the presence or absence of Bin2 and complex formation was assessed by SDS-PAGE and fluorography after immunoprecipitation with the Bin1 monoclonal antibody 99D [Wechsler-Reya et al., *Cancer Res.* 57: 3258–3263 (1997)].

Bin2 and Bin1 were in vitro translated with empty vector or cotranslated with each other in the presence of $^{35}$S-methionine. Products were fractionated on SDS-PAGE gels and fluorographed or subjected to immunoprecipitation with the anti-Bin1 antibody 99D [Wechsler-Reya et al., cited above] before fractionation. Bin2 migrated with an apparent MW 82 kD, which is greater than the predicted MW ~61 kD, reminiscent of a similar aberrent mobility displayed by Bin1, which has an apparent MW ~68 kD and a predicted MW ~50 kD. Bin2 was not immunoprecipitated by 99D unless cotranslated with Bin1.

Using a set of deletion mutants (Δ124–207, Δ1–122, Δ152–207, Δ143–148) the BAR domain in Bin1 was demonstrated to be required for Bin2 interaction. Deletion of the C-terminal region of BAR decreased binding efficiency, whereas deletion of residues 143–148 within a loop region implicated in effector signaling and representing the most highly conserved part of the BAR domain in Bin1 bad no effect. Deletion of the N-terminal region of BAR (residues 1–122) eliminated binding completely, arguing that the N-terminus of Bin1 was crucial for interaction with Bin2. Other deletion mutants of Bin1 lacking the so-called Unique central region, the Myc-binding domain, or the SH3 domain, interacted with Bin2 with the same efficiency as wild-type Bin1 (data not shown). It was concluded that Bin1 and Bin2 formed a BAR domain-dependent complex in cells.

Bin1 and Bin2 were shown to form a stable biochemical complex, in the manner of RVS161 and RVS167 in yeast or amphiphysin and neuronal splice isoforms of Bin1 in mammalian cells [Navarro et al., cited above (1997); Wigge et al., cited above (1997)], and the association depended upon the integrity of the BAR domain. Bin2 did not affect the tumor suppressor properties of Bin1 that are manifested in HepG2 cells [Sakamuro et al., *Nature Genet.* 14: 69–77 (1996)]. This may reflect different requirements for each activity, since Bin2 association rested on an N-terminal BAR determinant whereas the tumor suppressor activity of Bin1 rests upon a C-terminal BAR determinant. Evidence that BAR domains encode unique activities and are not functionally equivalent is provided by domain swapping studies performed in yeast [Sivadon et al., *FEBS Lett.* 417: 21–27 (1997)]. Thus, the BAR domain of Bin2 may have unique features, perhaps related to Bin1 regulation rather than effector signaling. In future work, it will be important to determine the physiological functions of Bin2 and how they are manifested independently or in an integrated manner with the functions of Bin1.

EXAMPLE 6

BIN2 Lacks In Vitro Growth Inhibitory Properties

Bin1 has tumor suppressor properties in certain malignant cells [Sakamuro et al. 1996, cited above], so whether Bin2 had any similar effects and/or whether it could influence the growth inhibitory activity of Bin1 was investigated. HepG2 hepatoma cells lack endogenous Bin1 and Bin2 expression so they provided a useful background to perform these experiments. Another cell line which lacks Bin2 expression, A549 lung carcinoma cells, was also used in these experiments. Cells were transfected with the same expression vector used above, which carries a neomycin resistance cassette, and stably transformed cells were selected in growth media containing G418.

Figure 5A:
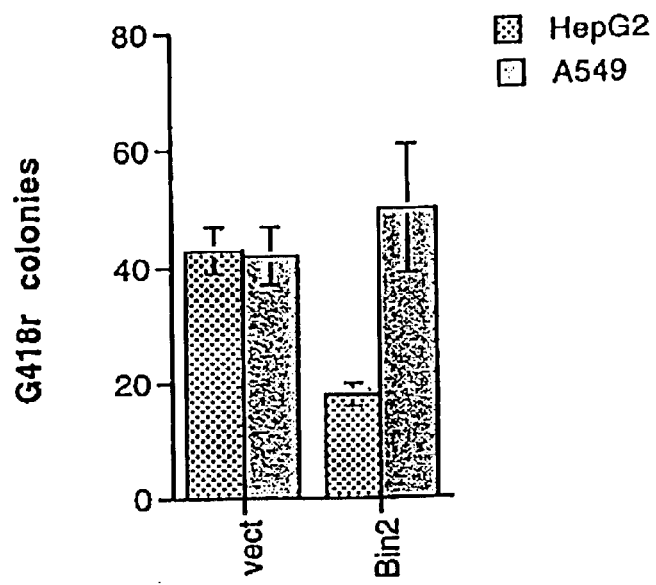
FIG. 5A is a bar graph illustrating the results of a colony formation assay. HepG2 and A549 cells were transfected with expression vectors and stable transformants were selected by culturing cells in G418. Colonies were scored by methanol fixation and crystal violet staining 2–3 weeks later. The data represent the mean and standard error from three trials.
Figure 5B:
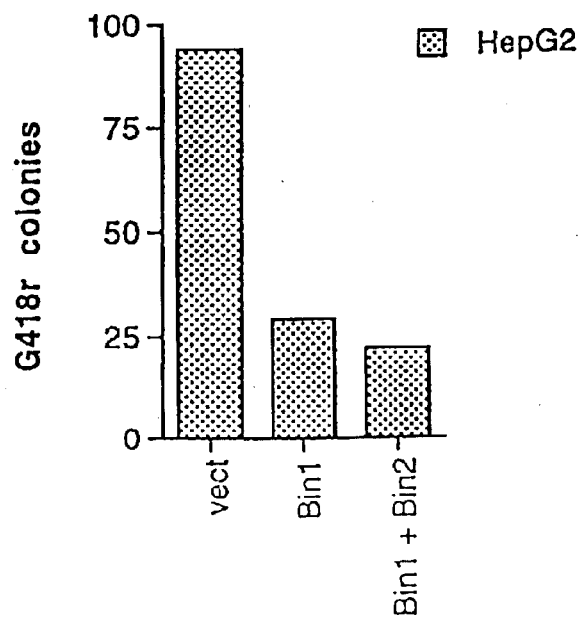
FIG. 5B is a bar graph that illustrates that Bin2 does not affect the tumor suppressor activity of Bin1. The colony formation assay was performed as above using 10 $\mu$g vector, 5 $\mu$g vector +5 $\mu$g Bin1 plasmid, or 5 $\mu$g Bin1+5 $\mu$g Bin2 plasmids.

A ~2-fold decrease in colony formation efficiency relative to empty vector was noted in HepG2 cells but not in A549 cells (see FIG. 5A). These observations suggested that Bin2 may be weakly growth inhibitory. To confirm this, HepG2 colonies were ring-cloned, expanded into cell lines, and examined for ectopic Bin2 expression by Northern analysis. For Northern analysis, total cytoplasmic RNA was isolated from colonies that were ring-cloned and expanded into cell lines. Northern analysis was performed using Bin2 cDNA as probe. Robust levels of Bin2 mRNA were detected in several independent cell lines which did not exhibit any signs of growth inhibition, confirming that accumulation of Bin message was compatible with HcpG2 proliferation To determine if Bin2 could relieve or augment growth suppression by Bin1, a similar set of colony formation experiments was performed in HepG2 except that untagged empty vector or Bin2 vector was cotransfected with a neomycin resistance gene-tagged Bin1 vector [Sakamuro et al. 1996, cited above]. The number of colonies which emerged using Bin2 vectors was similar to those produced with control vector, indicating that Bin2 did not affect the ability of Bin1 to suppress HepG2 cell growth (see FIG. 5B). It was concluded that Bin2 lacked the strong growth inhibitory properties in Hep G2 cells that are inherent to Bin1.

All above-noted references and priority document are incorporated herein by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. An isolated Bridging Integrator-2 (Bin2) protein having the amino acid sequence of SEQ ID NO: 2.

2. The Bin2 peptide or protein according to claim 1 selected from the group consisting of:

(a) amino acid sequence of SEQ ID NO: 2 with conservative amino acid substitution thereof; and (b) a fusion protein comprising the amino acid sequence of (a) or (b) and a fusion partner; and (c) a fusion protein comprising the amino acid sequence of SEQ ID NO: 2 and a fusion partner.

3. An isolated Bridging Integrator-2 (Bin21 peptide having the sequence of amino acids 1 to 221 of SEQ ID NO: 2.

4. The Bin2 protein according to claim 2, wherein the fusion partner is selected from the group consisting of glutationine-S-transferase, β-galactosidase, poly-histidine and maltose binding protein.

5. A composition comprising the Bin2 protein of claim 1 or claim 2 and a pharmaceutically acceptable carrier.

* * * * *

UNITED STATES PATENT AND TRADEMARK OFFICE
CERTIFICATE OF CORRECTION

PATENT NO. : 6,831,063 B1
DATED : December 14, 2004
INVENTOR(S) : George C. Prendergast and Kai Ge It is certified that error appears in the above-identified patent and that said Letters Patent is hereby corrected as shown below:

Column 1,
Line 42, replace "[Sakamuro et al" with -- [Sakarmuno et al --.

Column 2,
Line 57, replace "provides" with -- provided --.

Column 3,
Line 9, replace "Bia2" with -- Bin2 --.

Column 4,
Line 15, replace "Daxn" with -- Daxx --.

Column 6,
Line 27, replace "Instill" with -- In still --.
Line 64, replace "tern" with -- term --.

Column 8,
Line 2, replace "homolog" with -- "homology" --.

Column 9,
Line 20, replace "bioavailability," with -- bioavailability, --.
Line 48, replace "and/orto" with -- and/or to --.
Line 50, replace "an" with -- art --.

Column 10,
Line 48, replace "an." with -- art --.
Line 51, replace "of al," with -- et al --.
Line 55, replace "FIBlOl," with -- HB101, --.
Lines 65, 66, 67, delete "Alternatively, insect cells such as Spodoptera Frugipedera (Sf9) cells may be used, e.g. in the baculovirus expression system".

Column 11,
Lines 23, replace "(β-alactosidase, glutatliione-S-" with
-- β-galactosidase, glutathione-S- --.
Line 26, replace "vitao," with -- vivo --.

Column 12,
Line 48, replace "IMB" with -- TMB --.

UNITED STATES PATENT AND TRADEMARK OFFICE
CERTIFICATE OF CORRECTION

PATENT NO. : 6,831,063 B1
DATED : December 14, 2004
INVENTOR(S) : George C. Prendergast and Kai Ge It is certified that error appears in the above-identified patent and that said Letters Patent is hereby corrected as shown below:

Column 13,
Line 39, replace "Bind" with -- Bin2 --.

Column 14,
Line 12, replace "ccntrifugation," with -- centrifugation, --.
Line 32, replace "(a Hulg)" with -- (α Hulg) --.

Column 15,
Line 4, replace "Bid" with -- Bin2 --.
Line 45, replace "hematopoictic," with -- hematopoietic --.
Line 50, replace "BVV 173" with -- BV 173 --.

Column 16,
Line 15, replace "distcarate" with -- distearate --.

Column 18,
Line 63, replace "SlH3" with -- SH3 --.
Line 67, replace "normeuronal" with -- nonneuronal --.

Column 19,
Line 15, replace "4q221" with -- 4q22.1 --.
Line 22, replace "pseudoene" with -- pseudogene --.

Column 20,
Line 27, replace "296300" with -- 296-300 --.
Line 34, replace "Bin)" with -- Bin2) --.
Line 65, replace "the" with -- of the --.

Column 21,
Line 17, replace "(I 998);" with -- (1998); --.
Line 26, replace "[Quignonce at." with -- [Quignonce et al --.

Column 22,
Line 11, replace "hematopoictic" with -- hematopoietic --.
Line 23, replace "promyclocytic" with -- promyelocytic --.

Column 23,
Line 6, replace "communoprecipitation" with -- coimmunoprecipitation --.
Line 13, replace "$^{35}$S-" with -- 35S- --.
Line 18, replace "MW 82 kD," with -- MW~82kD, --.

UNITED STATES PATENT AND TRADEMARK OFFICE
CERTIFICATE OF CORRECTION

PATENT NO. : 6,831,063 B1
DATED : December 14, 2004
INVENTOR(S) : George C. Prendergast and Kai Ge It is certified that error appears in the above-identified patent and that said Letters Patent is hereby corrected as shown below:

Column 24.
Line 33, replace "HcpG2 proliferation" with -- HepG2 proliferation. --.

Column 33,
Line 46, delete "peptide or".
Line 51, delete "and".
Line 53, delete "or (b)".

Column 34,
Line 45, replace "(Bin21" with -- (Bin2) --.

Signed and Sealed this

Twenty-sixth Day of July, 2005

JON W. DUDAS
*Director of the United States Patent and Trademark Office*

SEQUENCE LISTING

<160> NUMBER OF SEQ ID NOS: 4

<210> SEQ ID NO 1
<211> LENGTH: 2196
<212> TYPE: DNA
<213> ORGANISM: Homo sapiens
<220> FEATURE:
<221> NAME/KEY: CDS
<222> LOCATION: (28)..(1719)
<223> OTHER INFORMATION:
<220> FEATURE:

<221> NAME/KEY: misc_feature
<222> LOCATION: (2032)..(2032)
<223> OTHER INFORMATION: can be a or c or g or t

<400> SEQUENCE: 1

```
gcggccgcgt cgacgggagt tgcagg atg gca gag ggc aag gca ggc ggc gcg        54
                             Met Ala Glu Gly Lys Ala Gly Gly Ala
                               1               5 gcc ggc ctc ttc gcc aag cag gtg cag aag aag ttt agc agg gcc cag        102
Ala Gly Leu Phe Ala Lys Gln Val Gln Lys Lys Phe Ser Arg Ala Gln
 10                  15                  20                  25 gag aag gtg ctg cag aaa ttg ggg aaa gct gta gaa acc aaa gat gaa        150
Glu Lys Val Leu Gln Lys Leu Gly Lys Ala Val Glu Thr Lys Asp Glu
                 30                  35                  40 cga ttt gaa caa agc gct agc aac ttc tac caa caa cag gca gaa ggc        198
Arg Phe Glu Gln Ser Ala Ser Asn Phe Tyr Gln Gln Gln Ala Glu Gly
                     45                  50                  55 cac aag ctg tac aag gac ctg aag aac ttc ctt agt gca gtc aaa gtg        246
His Lys Leu Tyr Lys Asp Leu Lys Asn Phe Leu Ser Ala Val Lys Val
                         60                  65                  70 atg cat gaa agt tca aaa aga gtg tca gaa acc ctg cag gag atc tac        294
Met His Glu Ser Ser Lys Arg Val Ser Glu Thr Leu Gln Glu Ile Tyr
 75                  80                  85 agc agc gag tgg gac ggt cat gag gag ctg aag gcc atc gta tgg aat        342
Ser Ser Glu Trp Asp Gly His Glu Glu Leu Lys Ala Ile Val Trp Asn
 90                  95                 100                 105 aat gat ctc ctt tgg gaa gac tac gag gag aaa ctg gct gac cag gct        390
Asn Asp Leu Leu Trp Glu Asp Tyr Glu Glu Lys Leu Ala Asp Gln Ala
                110                 115                 120 gta agg acc atg gaa atc tat gtt gcc cag ttc agt gaa att aag gag        438
Val Arg Thr Met Glu Ile Tyr Val Ala Gln Phe Ser Glu Ile Lys Glu
                125                 130                 135 aga att gcc aag cgg ggt cgg aaa ctc gtg gac tat gac agt gcc cga        486
Arg Ile Ala Lys Arg Gly Arg Lys Leu Val Asp Tyr Asp Ser Ala Arg
                140                 145                 150 cac cac ctg gag gca gtg cag aat gcc aag aaa gat gag gcc aag act        534
His His Leu Glu Ala Val Gln Asn Ala Lys Lys Asp Glu Ala Lys Thr
                155                 160                 165 gcc aag gca gag gaa gag ttc aac aaa gcc cag act gtg ttt gaa gat        582
Ala Lys Ala Glu Glu Glu Phe Asn Lys Ala Gln Thr Val Phe Glu Asp
170                 175                 180                 185 ctg aac caa gaa cta cta gag gag ctg cct att ctt tat aat agt cgt        630
Leu Asn Gln Glu Leu Leu Glu Glu Leu Pro Ile Leu Tyr Asn Ser Arg
                190                 195                 200 att ggc tgc tat gtg acc atc ttc caa aac att tcc aac ttg agg gat        678
Ile Gly Cys Tyr Val Thr Ile Phe Gln Asn Ile Ser Asn Leu Arg Asp
                205                 210                 215 gtc ttc tac agg gaa atg agc aag ctg aac cac aat ctc tac gag gtg        726
Val Phe Tyr Arg Glu Met Ser Lys Leu Asn His Asn Leu Tyr Glu Val
                220                 225                 230 atg agc aaa ctg gag aag caa cat tcc aat aaa gtc ttt gtg gtg aag        774
Met Ser Lys Leu Glu Lys Gln His Ser Asn Lys Val Phe Val Val Lys
235                 240                 245 gga ctg tca agc agc agc agg cgc tct tta gtc att tct ccc cca gtt        822
Gly Leu Ser Ser Ser Ser Arg Arg Ser Leu Val Ile Ser Pro Pro Val
250                 255                 260                 265 cga aca gct aca gtc tcc agt cct ctt acc tca cct act agt ccc tct        870
Arg Thr Ala Thr Val Ser Ser Pro Leu Thr Ser Pro Thr Ser Pro Ser
                270                 275                 280 aca ctt tcc ttg aag agt gag agt gaa tct gtc tca gca act gaa gat        918
Thr Leu Ser Leu Lys Ser Glu Ser Glu Ser Val Ser Ala Thr Glu Asp
```

-continued

```
Thr Leu Ser Leu Lys Ser Glu Ser Glu Ser Val Ser Ala Thr Glu Asp
            285                 290                 295 ctg gca cct gat gca gcc caa ggg gaa gac aat tct gag atc aag gag      966
Leu Ala Pro Asp Ala Ala Gln Gly Glu Asp Asn Ser Glu Ile Lys Glu
        300                 305                 310 ctc tta gaa gag gag gaa ata gag aag gaa gga tct gaa gca agc tcc     1014
Leu Leu Glu Glu Glu Glu Ile Glu Lys Glu Gly Ser Glu Ala Ser Ser
    315                 320                 325 tct gag gaa gat gac cct cta cca gcc tgc aat ggc ccc gcc cag gcc     1062
Ser Glu Glu Asp Asp Pro Leu Pro Ala Cys Asn Gly Pro Ala Gln Ala
330                 335                 340                 345 cag ccc tct cct acc act gag agg gcc aag tcc cag gag gaa gtt ctc     1110
Gln Pro Ser Pro Thr Thr Glu Arg Ala Lys Ser Gln Glu Glu Val Leu
                350                 355                 360 ccc agc tcc aca act cca tca cca ggc gga gcc ctg agc cct tca ggg     1158
Pro Ser Ser Thr Thr Pro Ser Pro Gly Gly Ala Leu Ser Pro Ser Gly
            365                 370                 375 cag cct tca tca tct gcc aca gaa gta gtc ctc cga acc cgc acc gca     1206
Gln Pro Ser Ser Ser Ala Thr Glu Val Val Leu Arg Thr Arg Thr Ala
        380                 385                 390 agt gaa gga tct gaa caa cca aag aag aga gcc tct atc cag agg acc     1254
Ser Glu Gly Ser Glu Gln Pro Lys Lys Arg Ala Ser Ile Gln Arg Thr
    395                 400                 405 tca gca ccc cct agt agg cct cct cca ccc aga gcc act gca agc ccc     1302
Ser Ala Pro Pro Ser Arg Pro Pro Pro Pro Arg Ala Thr Ala Ser Pro
410                 415                 420                 425 agg ccc tcc tca ggg aac ata cct tcc agc cct aca gcc tct gga ggg     1350
Arg Pro Ser Ser Gly Asn Ile Pro Ser Ser Pro Thr Ala Ser Gly Gly
                430                 435                 440 ggt tca ccc acc agc cct agg gcc tcc ttg ggg act ggg act gca agt     1398
Gly Ser Pro Thr Ser Pro Arg Ala Ser Leu Gly Thr Gly Thr Ala Ser
            445                 450                 455 cct agg acc tcc cta gag gtc tct cct aat cca gaa cca cca gag aag     1446
Pro Arg Thr Ser Leu Glu Val Ser Pro Asn Pro Glu Pro Pro Glu Lys
        460                 465                 470 cca gta aga act cct gag gcc aaa gaa aat gaa aac atc cac aat cag     1494
Pro Val Arg Thr Pro Glu Ala Lys Glu Asn Glu Asn Ile His Asn Gln
    475                 480                 485 aac cct gaa gaa ctt tgt act tcc ccc acc tta atg aca tct cag gtt     1542
Asn Pro Glu Glu Leu Cys Thr Ser Pro Thr Leu Met Thr Ser Gln Val
490                 495                 500                 505 gct tca gag cct gga gag gca aag aag atg gaa gac aag gaa aag gat     1590
Ala Ser Glu Pro Gly Glu Ala Lys Lys Met Glu Asp Lys Glu Lys Asp
                510                 515                 520 aat aag ctt atc tca gct gac tcc tcg gag ggc caa gac cag ctt caa     1638
Asn Lys Leu Ile Ser Ala Asp Ser Ser Glu Gly Gln Asp Gln Leu Gln
            525                 530                 535 gtc tcc atg gta cca gaa aac aac aac ctc aca gca cct gaa cct caa     1686
Val Ser Met Val Pro Glu Asn Asn Asn Leu Thr Ala Pro Glu Pro Gln
        540                 545                 550 gaa gag gta tcc aca agt gaa aat cca caa ctc tgaagagaaa ctaccaagac  1739
Glu Glu Val Ser Thr Ser Glu Asn Pro Gln Leu
    555                 560 tcctcctgcc ccaaacctcg ccagagaagc tcttcaacca gagggtatag gtcagaggga  1799
tataagagcc agcatccatc cctgggttct cagtaggaat gctggtgctg tctaaagacc  1859
tggcattaat ggaggcggag gagcagcctt acgggaggga tggagggagg caggctgggg  1919
agaagagaac attagactca gggaatattt aattctggtt ttagcattat tagaataaga  1979
```

```
ctttatacat taactaaagt ggagctttaa tcactataaa aagcaaaagt atntatagac    2039
acagacactt gcctatacag agacataacc acacacactc agaggatagt gaacaaatct    2099
gtctttgact tacgacccat tttgcaagac ttaaagccga agaacacat tttcagattg     2159 ttaaataaag tctgattctg actaaaaaaa aaaaaaa                             2196
```

<210> SEQ ID NO 2
<211> LENGTH: 564
<212> TYPE: PRT
<213> ORGANISM: Homo sapiens

<400> SEQUENCE: 2

```
Met Ala Glu Gly Lys Ala Gly Ala Ala Gly Leu Phe Ala Lys Gln
 1               5                  10                  15

Val Gln Lys Lys Phe Ser Arg Ala Gln Glu Lys Val Leu Gln Lys Leu
                20                  25                  30

Gly Lys Ala Val Glu Thr Lys Asp Glu Arg Phe Glu Gln Ser Ala Ser
                35                  40                  45

Asn Phe Tyr Gln Gln Ala Glu Gly His Lys Leu Tyr Lys Asp Leu
        50                  55                  60

Lys Asn Phe Leu Ser Ala Val Lys Val Met His Glu Ser Ser Lys Arg
65                  70                  75                  80

Val Ser Glu Thr Leu Gln Glu Ile Tyr Ser Ser Glu Trp Asp Gly His
                85                  90                  95

Glu Glu Leu Lys Ala Ile Val Trp Asn Asn Asp Leu Leu Trp Glu Asp
                100                 105                 110

Tyr Glu Glu Lys Leu Ala Asp Gln Ala Val Arg Thr Met Glu Ile Tyr
                115                 120                 125

Val Ala Gln Phe Ser Glu Ile Lys Glu Arg Ile Ala Lys Arg Gly Arg
                130                 135                 140

Lys Leu Val Asp Tyr Asp Ser Ala Arg His His Leu Glu Ala Val Gln
145                 150                 155                 160

Asn Ala Lys Lys Asp Glu Ala Lys Thr Ala Lys Ala Glu Glu Phe
                165                 170                 175

Asn Lys Ala Gln Thr Val Phe Glu Asp Leu Asn Gln Glu Leu Leu Glu
                180                 185                 190

Glu Leu Pro Ile Leu Tyr Asn Ser Arg Ile Gly Cys Tyr Val Thr Ile
                195                 200                 205

Phe Gln Asn Ile Ser Asn Leu Arg Asp Val Phe Tyr Arg Glu Met Ser
                210                 215                 220

Lys Leu Asn His Asn Leu Tyr Glu Val Met Ser Lys Leu Glu Lys Gln
225                 230                 235                 240

His Ser Asn Lys Val Phe Val Val Lys Gly Leu Ser Ser Ser Ser Arg
                245                 250                 255

Arg Ser Leu Val Ile Ser Pro Val Arg Thr Ala Thr Val Ser Ser
                260                 265                 270

Pro Leu Thr Ser Pro Thr Ser Pro Thr Leu Ser Leu Lys Ser Glu
                275                 280                 285

Ser Glu Ser Val Ser Ala Thr Glu Asp Leu Ala Pro Asp Ala Ala Gln
                290                 295                 300

Gly Glu Asp Asn Ser Glu Ile Lys Glu Leu Leu Glu Glu Glu Ile
305                 310                 315                 320

Glu Lys Glu Gly Ser Glu Ala Ser Ser Ser Glu Glu Asp Asp Pro Leu
                325                 330                 335
```

```
Pro Ala Cys Asn Gly Pro Ala Gln Ala Gln Pro Ser Pro Thr Thr Glu
            340                 345                 350

Arg Ala Lys Ser Gln Glu Val Leu Pro Ser Ser Thr Thr Pro Ser
            355                 360                 365

Pro Gly Gly Ala Leu Ser Pro Ser Gly Gln Pro Ser Ser Ser Ala Thr
            370                 375                 380

Glu Val Val Leu Arg Thr Arg Thr Ala Ser Glu Gly Ser Glu Gln Pro
385                 390                 395                 400

Lys Lys Arg Ala Ser Ile Gln Arg Thr Ser Ala Pro Pro Ser Arg Pro
                405                 410                 415

Pro Pro Pro Arg Ala Thr Ala Ser Pro Arg Pro Ser Ser Gly Asn Ile
            420                 425                 430

Pro Ser Ser Pro Thr Ala Ser Gly Gly Ser Pro Thr Ser Pro Arg
            435                 440                 445

Ala Ser Leu Gly Thr Gly Thr Ala Ser Pro Arg Thr Ser Leu Glu Val
450                 455                 460

Ser Pro Asn Pro Glu Pro Glu Lys Pro Val Arg Thr Pro Glu Ala
465                 470                 475                 480

Lys Glu Asn Glu Asn Ile His Asn Gln Asn Pro Glu Glu Leu Cys Thr
                485                 490                 495

Ser Pro Thr Leu Met Thr Ser Gln Val Ala Ser Glu Pro Gly Glu Ala
                500                 505                 510

Lys Lys Met Glu Asp Lys Glu Lys Asp Asn Lys Leu Ile Ser Ala Asp
            515                 520                 525

Ser Ser Glu Gly Gln Asp Gln Leu Gln Val Ser Met Val Pro Glu Asn
            530                 535                 540

Asn Asn Leu Thr Ala Pro Glu Pro Gln Glu Glu Val Ser Thr Ser Glu
545                 550                 555                 560

Asn Pro Gln Leu

<210> SEQ ID NO 3
<211> LENGTH: 252
<212> TYPE: PRT
<213> ORGANISM: Homo sapiens

<400> SEQUENCE: 3

Met Ala Glu Met Gly Ser Lys Gly Val Thr Ala Gly Lys Ile Ala Ser
1               5                   10                  15

Asn Val Gln Lys Lys Leu Thr Arg Ala Gln Glu Lys Val Leu Gln Lys
            20                  25                  30

Leu Gly Lys Ala Asp Glu Thr Lys Asp Glu Gln Phe Glu Gln Cys Val
        35                  40                  45

Gln Asn Phe Asn Lys Gln Leu Thr Glu Gly Thr Arg Leu Gln Lys Asp
    50                  55                  60

Leu Arg Thr Tyr Leu Ala Ser Val Lys Ala Met His Glu Ala Ser Lys
65                  70                  75                  80

Lys Leu Asn Glu Cys Leu Gln Glu Val Tyr Glu Pro Asp Trp Pro Gly
                85                  90                  95

Arg Asp Glu Ala Asn Lys Ile Ala Glu Asn Asn Asp Leu Leu Trp Met
                100                 105                 110

Asp Tyr His Gln Lys Leu Val Asp Gln Ala Leu Leu Thr Met Asp Thr
            115                 120                 125

Tyr Leu Gly Gln Phe Pro Asp Ile Lys Ser Arg Ile Ala Lys Arg Gly
        130                 135                 140
```

```
Arg Lys Leu Val Asp Tyr Asp Ser Ala Arg His His Tyr Glu Ser Leu
145                 150                 155                 160

Gln Thr Ala Lys Lys Lys Asp Glu Ala Lys Ile Ala Lys Ala Glu Glu
                165                 170                 175

Glu Leu Ile Lys Ala Gln Lys Val Phe Glu Glu Met Asn Val Asp Leu
            180                 185                 190

Gln Glu Glu Leu Pro Ser Leu Trp Asn Ser Arg Val Gly Phe Tyr Val
        195                 200                 205

Asn Thr Phe Gln Ser Ile Ala Gly Leu Glu Glu Asn Phe His Lys Glu
        210                 215                 220

Met Ser Lys Leu Asn Gln Asn Leu Asn Asp Val Leu Val Gly Leu Glu
225                 230                 235                 240

Lys Gln His Gly Ser Asn Thr Phe Thr Val Lys Ala
                245                 250

<210> SEQ ID NO 4
<211> LENGTH: 87
<212> TYPE: PRT
<213> ORGANISM: Homo sapiens

<400> SEQUENCE: 4

Ala Gln Asp Ala Phe Arg Asp Val Gly Ile Arg Leu Gln Glu Arg Arg
1               5                   10                  15

His Leu Asp Leu Ile Tyr Asn Phe Gly Cys His Leu Thr Asp Asp Tyr
            20                  25                  30

Arg Pro Gly Val Asp Pro Ala Leu Ser Tyr Pro Val Ser Ala Arg Arg
        35                  40                  45

Leu Arg Glu Asn Arg Ile Leu Ala Leu Ser Arg Leu Asp Gln Val Ile
    50                  55                  60

Ser Phe Tyr Ala Met Leu Gln Asp Gly Gly Glu Gly Lys Lys Lys
65                  70                  75                  80

Lys Arg Arg Ala Arg Leu Asp
                85
```